(12) United States Patent
Carlton et al.

(10) Patent No.: US 10,434,302 B2
(45) Date of Patent: Oct. 8, 2019

(54) DIRECTIONAL ELECTRODE DEVICES WITH LOCATING FEATURES

(71) Applicant: Intelect Medical Inc., Marlborough, MA (US)

(72) Inventors: Keith Carlton, Boston, MA (US); Alan Greszler, Bay Village, OH (US); Scott Kokones, Boston, MA (US)

(73) Assignee: INTELECT MEDICAL, INC., Cleveland, OH (US)

( * ) Notice: Subject to any disclaimer, the term of this patent is extended or adjusted under 35 U.S.C. 154(b) by 209 days.

(21) Appl. No.: 14/943,857

(22) Filed: Nov. 17, 2015

(65) Prior Publication Data

US 2016/0101279 A1  Apr. 14, 2016

Related U.S. Application Data

(62) Division of application No. 12/029,141, filed on Feb. 11, 2008, now Pat. No. 9,220,889.

(51) Int. Cl.
*A61N 1/05* (2006.01)
*A61N 1/36* (2006.01)

(52) U.S. Cl.
CPC ......... *A61N 1/0529* (2013.01); *A61N 1/0534* (2013.01); *A61N 1/0539* (2013.01); *A61N 1/36182* (2013.01); *A61N 1/0551* (2013.01)

(58) Field of Classification Search
CPC ....... A61N 1/05; A61N 1/0551; A61N 1/0539
See application file for complete search history.

(56) References Cited

U.S. PATENT DOCUMENTS 3,999,555 A   12/1976  Person
4,144,889 A    3/1979  Tyers et al.
(Continued)

FOREIGN PATENT DOCUMENTS

EP   0832667   4/1998
EP   1048320  11/2000
(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.
(Continued)

*Primary Examiner* — Michael J D Abreu
(74) *Attorney, Agent, or Firm* — Lowe Graham Jones PLLC; Bruce E. Black

(57) ABSTRACT

Electrode devices having directional electrodes for use in deep brain stimulation or other uses. In one aspect, an electrode assembly comprises an elongate lead and a lead guide that are engageable with each other in a coaxial relationship. When the elongate lead and the lead guide are engaged with each other, the two components are rotationally fixed in relation to each other. In another aspect, an elongate lead comprises a radiologically-visible feature for indicating the orientation of the elongate lead. In yet another aspect, an electrode system is capable of determining the position and/or orientation of an electrode positioned within a body. In other aspects, methods for electrically stimulating a target site in the body are disclosed.

20 Claims, 11 Drawing Sheets

(56) References Cited

U.S. PATENT DOCUMENTS

| | | | |
|---|---|---|---|
| 4,177,818 A | 12/1979 | De Pedro | |
| 4,341,221 A | 7/1982 | Testerman | |
| 4,378,797 A | 4/1983 | Osterholm | |
| 4,445,500 A | 5/1984 | Osterholm | |
| 4,735,208 A | 4/1988 | Wyler et al. | |
| 4,765,341 A | 8/1988 | Mower et al. | |
| 4,841,973 A | 6/1989 | Stecker | |
| 5,067,495 A | 11/1991 | Brehm | |
| 5,099,846 A | 3/1992 | Hardy | |
| 5,127,403 A | 7/1992 | Brownlee | |
| 5,203,777 A * | 4/1993 | Lee | A61M 25/0108 600/435 |
| 5,222,494 A | 6/1993 | Baker, Jr. | |
| 5,255,693 A | 10/1993 | Dutcher | |
| 5,259,387 A | 11/1993 | dePinto | |
| 5,304,206 A | 4/1994 | Baker, Jr. et al. | |
| 5,344,438 A | 9/1994 | Testerman et al. | |
| 5,360,441 A | 11/1994 | Otten | |
| 5,361,763 A | 11/1994 | Kao et al. | |
| 5,452,407 A | 9/1995 | Crook | |
| 5,480,421 A | 1/1996 | Otten | |
| 5,522,875 A | 6/1996 | Gates et al. | |
| 5,560,360 A | 10/1996 | Filler et al. | |
| 5,565,949 A | 10/1996 | Kasha, Jr. | |
| 5,593,427 A | 1/1997 | Gliner et al. | |
| 5,601,612 A | 2/1997 | Gliner et al. | |
| 5,607,454 A | 3/1997 | Cameron et al. | |
| 5,620,470 A | 4/1997 | Gliner et al. | |
| 5,651,767 A | 7/1997 | Schulman et al. | |
| 5,711,316 A | 1/1998 | Elsberry et al. | |
| 5,713,922 A | 2/1998 | King | |
| 5,716,377 A | 2/1998 | Rise et al. | |
| 5,724,985 A | 3/1998 | Snell et al. | |
| 5,749,904 A | 5/1998 | Gliner et al. | |
| 5,749,905 A | 5/1998 | Gliner et al. | |
| 5,769,858 A | 6/1998 | Pearson et al. | |
| 5,776,170 A | 7/1998 | MacDonald et al. | |
| 5,782,762 A | 7/1998 | Vining | |
| 5,824,030 A | 10/1998 | Yang et al. | |
| 5,843,148 A | 12/1998 | Gijsbers et al. | |
| 5,859,922 A | 1/1999 | Hoffmann | |
| 5,868,740 A | 2/1999 | LeVeen et al. | |
| 5,897,583 A | 4/1999 | Meyer et al. | |
| 5,910,804 A | 6/1999 | Fortenbery et al. | |
| 5,925,070 A | 7/1999 | King et al. | |
| 5,938,688 A | 8/1999 | Schiff | |
| 5,938,690 A | 8/1999 | Law et al. | |
| 5,968,082 A * | 10/1999 | Heil | A61N 1/3752 607/37 |
| 5,978,713 A | 11/1999 | Prutchi et al. | |
| 6,016,449 A | 1/2000 | Fischell et al. | |
| 6,029,090 A | 2/2000 | Herbst | |
| 6,029,091 A | 2/2000 | de la Rama et al. | |
| 6,050,992 A | 4/2000 | Nichols | |
| 6,058,331 A | 5/2000 | King | |
| 6,066,163 A | 5/2000 | John | |
| 6,083,162 A | 7/2000 | Vining | |
| 6,094,598 A | 7/2000 | Elsberry et al. | |
| 6,096,756 A | 8/2000 | Crain et al. | |
| 6,106,460 A | 8/2000 | Panescu et al. | |
| 6,109,269 A | 8/2000 | Rise et al. | |
| 6,128,538 A | 10/2000 | Fischell et al. | |
| 6,129,685 A | 10/2000 | Howard, III | |
| 6,146,390 A | 11/2000 | Heilbrun et al. | |
| 6,161,044 A | 12/2000 | Silverstone | |
| 6,167,311 A | 12/2000 | Rezai | |
| 6,181,969 B1 | 1/2001 | Gord | |
| 6,192,266 B1 | 2/2001 | Dupree et al. | |
| 6,205,361 B1 | 3/2001 | Kuzma | |
| 6,208,881 B1 | 3/2001 | Champeau | |
| 6,240,308 B1 | 5/2001 | Hardy et al. | |
| 6,246,912 B1 | 6/2001 | Sluijter et al. | |
| 6,253,109 B1 | 6/2001 | Gielen | |
| 6,289,239 B1 | 9/2001 | Panescu et al. | |
| 6,301,492 B1 | 10/2001 | Zonenshayn | |
| 6,310,619 B1 | 10/2001 | Rice | |
| 6,319,241 B1 | 11/2001 | King | |
| 6,336,899 B1 | 1/2002 | Yamazaki | |
| 6,343,226 B1 | 1/2002 | Sunde et al. | |
| 6,351,675 B1 | 2/2002 | Tholen et al. | |
| 6,353,762 B1 | 3/2002 | Baudino et al. | |
| 6,366,813 B1 | 4/2002 | Dilorenzo | |
| 6,368,331 B1 | 4/2002 | Front et al. | |
| 6,389,311 B1 | 5/2002 | Whayne et al. | |
| 6,393,325 B1 | 5/2002 | Mann et al. | |
| 6,421,566 B1 | 7/2002 | Holsheimer | |
| 6,435,878 B1 | 8/2002 | Reynolds et al. | |
| 6,442,432 B2 | 8/2002 | Lee | |
| 6,463,328 B1 | 10/2002 | John | |
| 6,491,699 B1 | 12/2002 | Henderson et al. | |
| 6,494,831 B1 | 12/2002 | Koritzinsky | |
| 6,507,759 B1 | 1/2003 | Prutchi et al. | |
| 6,510,347 B2 | 1/2003 | Borkan | |
| 6,516,227 B1 | 2/2003 | Meadows et al. | |
| 6,517,480 B1 | 2/2003 | Krass | |
| 6,539,263 B1 | 3/2003 | Schiff | |
| 6,560,490 B2 | 5/2003 | Grill et al. | |
| 6,579,280 B1 | 6/2003 | Kovach et al. | |
| 6,600,956 B2 | 7/2003 | Maschino et al. | |
| 6,606,523 B1 | 8/2003 | Jenkins | |
| 6,609,029 B1 | 8/2003 | Mann et al. | |
| 6,609,031 B1 | 8/2003 | Law et al. | |
| 6,609,032 B1 | 8/2003 | Woods et al. | |
| 6,622,048 B1 | 9/2003 | Mann et al. | |
| 6,631,297 B1 | 10/2003 | Mo | |
| 6,654,642 B2 | 11/2003 | North et al. | |
| 6,662,053 B2 | 12/2003 | Borkan | |
| 6,675,046 B2 | 1/2004 | Holsheimer | |
| 6,684,106 B2 | 1/2004 | Herbst | |
| 6,687,392 B1 | 2/2004 | Touzawa et al. | |
| 6,690,972 B2 | 2/2004 | Conley et al. | |
| 6,690,974 B2 | 2/2004 | Archer et al. | |
| 6,692,315 B1 | 2/2004 | Soumillon et al. | |
| 6,694,162 B2 | 2/2004 | Hartlep | |
| 6,694,163 B1 | 2/2004 | Vining | |
| 6,708,096 B1 | 3/2004 | Frei et al. | |
| 6,741,892 B1 | 5/2004 | Meadows et al. | |
| 6,748,098 B1 | 6/2004 | Rosenfeld | |
| 6,748,276 B1 | 6/2004 | Daignault, Jr. et al. | |
| 6,778,846 B1 | 8/2004 | Martinez et al. | |
| 6,788,969 B2 | 9/2004 | Dupree et al. | |
| 6,795,737 B2 | 9/2004 | Gielen et al. | |
| 6,827,681 B2 | 12/2004 | Tanner et al. | |
| 6,830,544 B2 | 12/2004 | Tanner | |
| 6,845,267 B2 | 1/2005 | Harrison et al. | |
| 6,850,802 B2 | 2/2005 | Holsheimer | |
| 6,895,280 B2 | 5/2005 | Meadows et al. | |
| 6,909,913 B2 | 6/2005 | Vining | |
| 6,937,891 B2 | 8/2005 | Leinders et al. | |
| 6,937,903 B2 | 8/2005 | Schuler et al. | |
| 6,944,497 B2 | 9/2005 | Stypulkowski | |
| 6,944,501 B1 | 9/2005 | Pless | |
| 6,950,707 B2 | 9/2005 | Whitehurst | |
| 6,969,388 B2 | 11/2005 | Goldman et al. | |
| 7,003,349 B1 | 2/2006 | Andersson et al. | |
| 7,003,352 B1 | 2/2006 | Whitehurst | |
| 7,008,370 B2 | 3/2006 | Tanner et al. | |
| 7,008,413 B2 | 3/2006 | Kovach et al. | |
| 7,035,690 B2 | 4/2006 | Goetz | |
| 7,043,293 B1 | 5/2006 | Baura | |
| 7,047,082 B1 | 5/2006 | Schrom et al. | |
| 7,047,084 B2 | 5/2006 | Erickson et al. | |
| 7,050,855 B2 | 5/2006 | Zeijlemaker et al. | |
| 7,050,857 B2 | 5/2006 | Samuelsson et al. | |
| 7,054,692 B1 | 5/2006 | Whitehurst et al. | |
| 7,136,518 B2 | 5/2006 | Griffin et al. | |
| 7,058,446 B2 | 6/2006 | Schuler et al. | |
| 7,082,333 B1 | 7/2006 | Bauhahn et al. | |
| 7,107,102 B2 | 9/2006 | Daignault et al. | |
| 7,126,000 B2 | 10/2006 | Ogawa et al. | |
| 7,127,297 B2 | 10/2006 | Law et al. | |
| 7,136,695 B2 | 11/2006 | Pless et al. | |
| 7,142,923 B2 | 11/2006 | North et al. | |
| 7,146,219 B2 | 12/2006 | Sieracki et al. | |

(56) References Cited

U.S. PATENT DOCUMENTS

| | | | |
|---|---|---|---|
| 7,146,223 B1 | 12/2006 | King | |
| 7,151,961 B1 | 12/2006 | Whitehurst | |
| 7,155,279 B2 | 12/2006 | Whitehurst | |
| 7,167,760 B2 | 1/2007 | Dawant et al. | |
| 7,174,219 B2 | 2/2007 | Wahlstrand et al. | |
| 7,177,674 B2 | 2/2007 | Echauz et al. | |
| 7,181,286 B2 | 2/2007 | Sieracki et al. | |
| 7,181,288 B1 | 2/2007 | Rezai et al. | |
| 7,184,837 B2 | 2/2007 | Goetz | |
| 7,191,014 B2 | 3/2007 | Kobayashi et al. | |
| 7,209,787 B2 | 4/2007 | Dilorenzo | |
| 7,211,050 B1 | 5/2007 | Caplygin | |
| 7,216,000 B2 | 5/2007 | Sieracki et al. | |
| 7,217,276 B2 | 5/2007 | Henderson | |
| 7,218,968 B2 | 5/2007 | Condie et al. | |
| 7,228,179 B2 | 6/2007 | Campen et al. | |
| 7,231,254 B2 | 6/2007 | DiLorenzo | |
| 7,236,830 B2 | 6/2007 | Gliner | |
| 7,239,910 B2 | 7/2007 | Tanner | |
| 7,239,916 B2 | 7/2007 | Thompson et al. | |
| 7,239,926 B2 | 7/2007 | Goetz | |
| 7,242,984 B2 | 7/2007 | DiLorenzo | |
| 7,244,150 B1 | 7/2007 | Brase et al. | |
| 7,252,090 B2 | 8/2007 | Goetz | |
| 7,254,445 B2 | 8/2007 | Law et al. | |
| 7,254,446 B1 | 8/2007 | Erickson | |
| 7,257,447 B2 | 8/2007 | Cates et al. | |
| 7,266,412 B2 | 9/2007 | Stypulkowski | |
| 7,294,107 B2 | 11/2007 | Simon et al. | |
| 7,295,876 B1 | 11/2007 | Erickson | |
| 7,299,096 B2 | 11/2007 | Balzer et al. | |
| 7,308,302 B1 | 12/2007 | Schuler et al. | |
| 7,313,430 B2 | 12/2007 | Urquhart | |
| 7,324,851 B1 | 1/2008 | DiLorenzo | |
| 7,346,382 B2 | 3/2008 | McIntyre et al. | |
| 7,359,755 B2* | 4/2008 | Jones | A61B 17/3415 607/117 |
| 7,388,974 B2 | 6/2008 | Yanagita | |
| 7,437,193 B2 | 10/2008 | Parramon et al. | |
| 7,463,928 B2 | 12/2008 | Lee et al. | |
| 7,499,048 B2 | 3/2009 | Sieracki et al. | |
| 7,505,815 B2 | 3/2009 | Lee et al. | |
| 7,548,786 B2 | 6/2009 | Lee et al. | |
| 7,565,199 B2 | 7/2009 | Sheffield et al. | |
| 7,603,177 B2 | 10/2009 | Sieracki et al. | |
| 7,617,002 B2 | 11/2009 | Goetz | |
| 7,623,918 B2 | 11/2009 | Goetz | |
| 7,650,184 B2 | 1/2010 | Walter | |
| 7,657,319 B2 | 2/2010 | Goetz et al. | |
| 7,672,734 B2 | 3/2010 | Anderson et al. | |
| 7,676,273 B2 | 3/2010 | Goetz et al. | |
| 7,680,526 B2 | 3/2010 | McIntyre et al. | |
| 7,734,340 B2 | 6/2010 | De Ridder | |
| 7,761,165 B1 | 7/2010 | He et al. | |
| 7,822,483 B2* | 10/2010 | Stone | A61N 1/0529 607/116 |
| 7,826,902 B2 | 11/2010 | Stone et al. | |
| 7,848,802 B2 | 12/2010 | Goetz et al. | |
| 7,860,548 B2 | 12/2010 | McIntyre et al. | |
| 7,879,024 B2* | 2/2011 | Thorstenson | A61M 25/0668 604/103.1 |
| 7,904,134 B2 | 3/2011 | McIntyre et al. | |
| 7,945,105 B1 | 5/2011 | Jaenisch | |
| 7,949,395 B2 | 5/2011 | Kuzma | |
| 7,974,706 B2 | 7/2011 | Moffitt et al. | |
| 8,019,439 B2 | 9/2011 | Kuzma et al. | |
| 8,175,710 B2 | 5/2012 | He | |
| 8,180,601 B2 | 5/2012 | Butson et al. | |
| 8,195,300 B2 | 6/2012 | Gliner et al. | |
| 8,224,450 B2 | 7/2012 | Brase | |
| 8,257,684 B2 | 9/2012 | Covalin et al. | |
| 8,262,714 B2 | 9/2012 | Hulvershorn et al. | |
| 8,364,278 B2 | 1/2013 | Pianca et al. | |
| 8,429,174 B2 | 4/2013 | Ramani et al. | |
| 8,452,415 B2 | 5/2013 | Goetz et al. | |
| 8,543,189 B2 | 9/2013 | Paitel et al. | |
| 8,606,360 B2 | 12/2013 | Butson et al. | |
| 8,620,452 B2 | 12/2013 | King et al. | |
| 8,918,184 B1 | 12/2014 | Torgerson et al. | |
| 9,474,894 B2* | 10/2016 | Mercanzini | A61N 1/0534 |
| 2001/0031071 A1 | 10/2001 | Nichols et al. | |
| 2002/0032375 A1 | 3/2002 | Bauch et al. | |
| 2002/0062143 A1 | 5/2002 | Baudino et al. | |
| 2002/0087201 A1 | 7/2002 | Firlik et al. | |
| 2002/0099295 A1 | 7/2002 | Gil et al. | |
| 2002/0115603 A1 | 8/2002 | Whitehouse | |
| 2002/0116030 A1 | 8/2002 | Rezai | |
| 2002/0123780 A1 | 9/2002 | Grill et al. | |
| 2002/0128694 A1 | 9/2002 | Holsheimer | |
| 2002/0151939 A1 | 10/2002 | Rezai | |
| 2002/0183607 A1 | 12/2002 | Bauch et al. | |
| 2002/0183740 A1 | 12/2002 | Edwards et al. | |
| 2002/0183817 A1 | 12/2002 | Van Venrooij et al. | |
| 2003/0097159 A1 | 5/2003 | Schiff et al. | |
| 2003/0149450 A1 | 8/2003 | Mayberg | |
| 2003/0171791 A1 | 9/2003 | KenKnight et al. | |
| 2003/0212439 A1 | 11/2003 | Schuler et al. | |
| 2004/0034394 A1 | 2/2004 | Woods et al. | |
| 2004/0044279 A1 | 3/2004 | Lewin et al. | |
| 2004/0044378 A1 | 3/2004 | Holsheimer | |
| 2004/0044379 A1 | 3/2004 | Holsheimer | |
| 2004/0054297 A1 | 3/2004 | Wingeier et al. | |
| 2004/0059395 A1 | 3/2004 | North et al. | |
| 2004/0098074 A1 | 5/2004 | Erickson et al. | |
| 2004/0106916 A1 | 6/2004 | Quaid et al. | |
| 2004/0133248 A1 | 7/2004 | Frei et al. | |
| 2004/0152957 A1 | 8/2004 | Stivoric et al. | |
| 2004/0181262 A1 | 9/2004 | Bauhahn | |
| 2004/0186532 A1 | 9/2004 | Tadlock | |
| 2004/0199216 A1 | 10/2004 | Lee et al. | |
| 2004/0267330 A1 | 12/2004 | Lee et al. | |
| 2005/0021090 A1 | 1/2005 | Schuler et al. | |
| 2005/0033380 A1 | 2/2005 | Tanner et al. | |
| 2005/0049649 A1 | 3/2005 | Luders et al. | |
| 2005/0060001 A1 | 3/2005 | Singhal et al. | |
| 2005/0060009 A1 | 3/2005 | Goetz | |
| 2005/0070781 A1 | 3/2005 | Dawant et al. | |
| 2005/0075689 A1 | 4/2005 | Toy et al. | |
| 2005/0085714 A1 | 4/2005 | Foley et al. | |
| 2005/0165294 A1 | 7/2005 | Weiss | |
| 2005/0171587 A1* | 8/2005 | Daglow | A61N 1/0551 607/116 |
| 2005/0228250 A1 | 10/2005 | Bitter et al. | |
| 2005/0251061 A1 | 11/2005 | Schuler et al. | |
| 2005/0261061 A1 | 11/2005 | Nguyen et al. | |
| 2005/0261601 A1 | 11/2005 | Schuler et al. | |
| 2005/0261747 A1 | 11/2005 | Schuler et al. | |
| 2005/0267347 A1 | 12/2005 | Oster | |
| 2005/0288732 A1 | 12/2005 | Schuler et al. | |
| 2006/0004422 A1 | 1/2006 | De Ridder | |
| 2006/0017749 A1 | 1/2006 | McIntyre et al. | |
| 2006/0020292 A1 | 1/2006 | Goetz et al. | |
| 2006/0069415 A1 | 3/2006 | Cameron et al. | |
| 2006/0094951 A1 | 5/2006 | Dean et al. | |
| 2006/0095088 A1 | 5/2006 | De Ridder | |
| 2006/0155340 A1 | 7/2006 | Schuler et al. | |
| 2006/0206169 A1 | 9/2006 | Schuler | |
| 2006/0218007 A1 | 9/2006 | Bjorner et al. | |
| 2006/0224189 A1 | 10/2006 | Schuler et al. | |
| 2006/0235472 A1 | 10/2006 | Goetz et al. | |
| 2006/0259079 A1 | 11/2006 | King | |
| 2006/0259099 A1 | 11/2006 | Goetz et al. | |
| 2007/0000372 A1 | 1/2007 | Rezai et al. | |
| 2007/0017749 A1 | 1/2007 | Dold et al. | |
| 2007/0027514 A1 | 2/2007 | Gerber | |
| 2007/0043268 A1 | 2/2007 | Russell | |
| 2007/0049817 A1 | 3/2007 | Preiss et al. | |
| 2007/0067003 A1 | 3/2007 | Sanchez et al. | |
| 2007/0078498 A1 | 4/2007 | Rezai et al. | |
| 2007/0083104 A1 | 4/2007 | Butson et al. | |
| 2007/0123953 A1 | 5/2007 | Lee et al. | |
| 2007/0129769 A1 | 6/2007 | Bourget et al. | |
| 2007/0135855 A1 | 6/2007 | Foshee et al. | |
| 2007/0150036 A1 | 6/2007 | Anderson | |

(56) References Cited

U.S. PATENT DOCUMENTS

| | | |
|---|---|---|
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Buston et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0016378 A1* | 1/2012 | Pianca ............... A61N 1/0534 606/129 |
| 2012/0027272 A1 | 2/2012 | Akinyemi et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0166476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1166819 | 1/2002 |
| EP | 1372780 | 1/2004 |
| EP | 1559369 | 8/2005 |
| EP | 1602393 | 12/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2004 |
| WO | 20050053789 | 6/2005 |
| WO | WO-2005079911 A1 * | 9/2005 ........... A61N 1/0553 |
| WO | 2006017053 | 2/2006 |
| WO | 2006113305 | 10/2006 |
| WO | 20071097859 | 8/2007 |

(56) References Cited

FOREIGN PATENT DOCUMENTS

| WO | 20071097861 A1 | 8/2007 |
|---|---|---|
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Butson et al., "Current Steering to control the volume of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006).209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.

Rattay, F. "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45(6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }. (Nov. 1990), 1118-1120.

Rubinstein, J. T., et al., "Signal coding in cochlear implants: exploiting stochastic effects of electrical stimulation", Ann Otol Rhinol Laryngol Suppl . . . 191, (Sep. 2003), 14-9.

Schwan, H.P., et al., "The conductivity of living tissues.", Ann NY Acad Sci., 65(6). (AUQ., 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Geddes, L. A., et al., "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments-electrochemical considerations.", J Neurosci Methods, 142(2), (Mar. 30, 2005),251-65.

Vidailhet, M. , "Bilateral deep-brain stimulation of the globus pallidus in primary generalized dystonia", N Engl J Med. 352(5) (Feb. 3, 2005),459-67.

Izad, Oliver, "Computationally Efficient Method in Predicating Axonal Excitation," Dissertation for Master Degree, Department of Biomedical Engineering, Case Western Reserve University, May 2009.

Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi:10.1007/BF01908075.

Cover, T.M. et al., "Elements of information theory," (1991) John Wiley & Sons, New York, NY.

Meila, Marina, "Comparing Clusterings by the Variation of Information," Learning Theory and Kernel Machines (2003): 173-187.

Viola, P., et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Indroduction to the Programming of Deep Brain Stimulators, Movement Disorders, vol. 17, Suppl. 3. pp. S181-S187 (2002).

Miocinovic et al. "Cicerone: Stereotactic Neurophysiological Recording and Deep Brain Stimulation Electrode Placement Software System," Acta Neurochirugica Suppl., Jan. 1, 2007, vol. 97, No. 2, pp. 561-567.

Schmidt et al. "Sketching and Composing Widgets for 3D Manipulation," Eurographics, Apr. 2008. vol. 27. No. 2, pp. 301-310.

Volkmann, J. , et al., "Basic algorithms for the programming of deep brain stimulation in Parkinson's disease". Mov Disord., 21 Suppl 14. (Jun. 2006),S284-9.

Walter, B. L., et al., "Surgical treatment for Parkinson's disease", Lancet Neural, 3(12), (Dec. 2004),719-28.

Wei, X. F., et al., "Current density distributions, field distributions and impedance analysis of segmented deep brain stimulation electrodes", J Neural Eng . . . 2(4). (Dec. 2005), 139-47.

Zonenshayn, M. , et al., "Location of the active contact within the subthalamic nucleus (STN) in the treatment of idiopathic Parkinson's disease.", Surg Neurol., 62(3) (Sep. 2004),216-25.

Da Silva et al (A primer on diffusion tensor imaging of anatomical substructures. Neurosurg Focus 15(1): p. 1-4, Article 4, 2003.).

(56) References Cited

OTHER PUBLICATIONS

Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective nerual stimulation", IEEE Engineering in Medicine and Biology Magazine, 14(4), (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients. J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004 ),2755-63.
Montgomery, E. B., et al., "Mechanism of deep brain stimulation and future technical developments.", Neurol Res. 22(3). (Apr. 2000),259-66.
Merrill, D. R., et al., "Electrical stimulation of excitable tissue design of efficacious and safe protocols", J Neruosci Methods. 141(2), (Feb. 15, 2005), 171-98.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12:// www.sci.utah.edu/cibc/software/index.html. MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003), 1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.

Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular filed potentials and the frequency-filtering properties of extracellular space", Biophys J . . . 86(3), (Mar. 2004), 1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005), 196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

(56) References Cited

OTHER PUBLICATIONS

Levy, AL., et al., "An Internet-connected, patient-specific, deformable brain atlas integrated into a surgical navigation system," J Digit Imaging, 10(3 Suppl 1) (Aug. 1997), pp. 231-237.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Extracellular stimulation of central neurons: influence of stimulus waveform and frequency on neuronal output," J. Neurophysiol., 88(4), (Oct. 2002), pp. 1592-1604.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, Cameron C., et al., "Modeling the excitability of mammalian nerve fibers: influence of aflerpotentials on the recovery cycle," J Neurophysiol, 87(2) (Feb. 2002), pp. 995-1006.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59(5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys., 29(4) (Dec. 1967), pp. 657-664.

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes." Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The infiuence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

Sl. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

(56) References Cited

OTHER PUBLICATIONS

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001 ), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Wakana, S., et al., "Fiber tract-based atlas of human white matter anatomy," Radiology, 230(1) (Jan. 2004), pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.

Yianni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantable Microstimulators" ICM '98 Proceedings of the Tenth International Conference, pp. 67-70.

Butson, Christopher R. , et al., "Patient-specific analysis of the volume of tissue activated during deep brain stimulation", NeuroImage. vol. 34 (2007), 661-670.

Adler, DE., et al., "The tentorial notch: anatomical variation, morphometric analysis, and classification in 100 human autopsy cases," J. Neurosurg., 96(6), (Jun. 2002), pp. 1103-1112.

Jones et al., "An Advanced Demultiplexing System for Physiological Stimulation", IEEE Transactions on Biomedical Engineering, vol. 44 No. 12 Dec. 1997, pp. 1210-1220.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic implications," Movement Disorders, 17(5), (Sep./Oct. 2002), pp. 969-983.

Bammer, R, et al., "Diffusion tensor imaging using single-shot SENSE-EPI", Magn Reson Med., 48(1 ), (Jul. 2002), pp. 128-136.

Basser, P J., et al., "MR diffusion tensor spectroscopy and imaging," Biophys J., 66(1 ), (Jan. 1994), pp. 259-267.

Basser, P J., et al., "New currents in electrical stimulation of excitable tissues," Annu Rev Biomed Eng., 2, (2000), pp. 377-397.

Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.

Benabid, A L., et al., "Long-term suppression of tremor by chronic stimulation of the ventral intermediate thalamic nucleus," Lancet, 337 (8738), (Feb. 16, 1991 ), pp. 403-406.

Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.

Christensen, Gary E., et al., "Volumetric transformation of brain anatomy," IEEE Transactions on Medical Imaging, 16(6), (Dec. 1997), pp. 864-877.

Cooper, S , et al., "Differential effects of thalamic stimulation parameters on tremor and paresthesias in essential tremor," Movement Disorders, 17(Supp. 5), (2002), p. S193.

Coubes, P, et al., "Treatment of DYT1-generalised dystonia by stimulation of the internal globus pallidus," Lancet, 355(9222), (Jun. 24, 2000), pp. 2220-2221.

Dasilva, A.F. M., et al., "A Primer Diffusion Tensor Imaging of Anatomical Substructures," Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

Finnis, K. W., et al., "3D Functional atalas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.

Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.

Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

Finnis, K. W., et al., "Application of a Population Based Electrophysiological Database to the Planning and Guidance of Deep Brain Sterotactic Neurosurgery," Proceedings of the 5th International Conference on Medical Image Computing and Computer-Assisted Intervention—Part 11, Lecture Notres in Computer Science; vol. 2489 (2002), pp. 69-76.

Finnis, K. W., et al., "Subcortical physiology deformed into a patient-specific brain atlas for image-guided stereotaxy," Proceed-

(56) References Cited

OTHER PUBLICATIONS ings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L., et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.

Haueisen, J., et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.

(56) References Cited

OTHER PUBLICATIONS

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.
An, et al., "Prefronlal cortical projections to longitudinal columns in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T., et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421(2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: world-wide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The NEURON simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
McIntyre, Cameron , et al., "Finite element analysis of the current-density and electric field generated by metal microelectrodes", Ann Biomed Eng . 29(3), (2001 ),227-235.
Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med . . . 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000),45-50.
Hines, M. L., et al., "The Neuron simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S. , et al., "Evolution of Brain Impedance in Dystonic Patients Treated by GPi Electrical Stimulation", Neuromodulation 7(2) (Apr. 2004),67-75.

(56) References Cited

OTHER PUBLICATIONS

Hemm, S., et al., "Deep brain stimulation in movement disorders: stereotactic coregistration of two-dimensional electrical field modeling and magnetic resonance imaging.". J Neurosurg. 103(6), (Dec. 2005),949-55.

Haueisen, J, et al., "The influence of brain tissue anisotropy on human EEG and MEG", Neuroimage 15(1) (Jan. 2002),159-166.

Haslinger, B., et al., "Frequency-correlated decreases of motor cortex activity associated with subthalamic nucleus stimulation in Parkinson's disease.", Neuroimage 28(3). (Nov. 15, 2005),598-606.

Hashimoto, T. , et al., "Stimulation of the subthalamic nucleus changes the firing pattern of pallidal neurons,", J Neurosci. 23(5). (Mar. 1, 2003), 1916-23.

Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.

McNaughtan et al., "Electrochemical Issues in Impedance Tomography", 1st World Congress on Industrial Process Tomography, Buxton, Greater Manchester, Apr. 14-17, 1999.

Grill, WM., et al., "Electrical properties of implant encapsulation tissue", Ann Biomed Eng. vol. 22. (1994),23-33.

Grill, W. M., et al., "Deep brain stimulation creates an informational lesion of the stimulated nucleus", Neuroreport. 15I7t (May 19, 2004 ), 1137-40.

PCT International Search Report and Written Opinion dated Jul. 1, 2009.

Official Communication for U.S. Appl. No. 12/029,141 dated Jun. 5, 2015.

Official Communication for U.S. Appl. No. 12/029,141 dated Jan. 29, 2015.

Official Communication for U.S. Appl. No. 12/029,141 dated Jul. 8, 2014.

Official Communication for U.S. Appl. No. 12/029,141 dated Apr. 27, 2011.

Official Communication for U.S. Appl. No. 12/029,141 dated Aug. 27, 2010.

\* cited by examiner

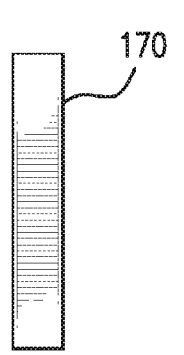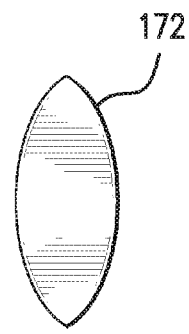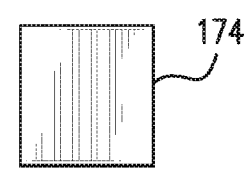
FIG.6A　　FIG.6B　　FIG.6C
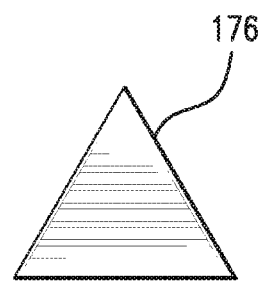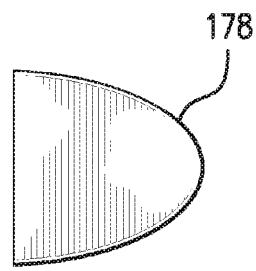
FIG.6D　　FIG.6E

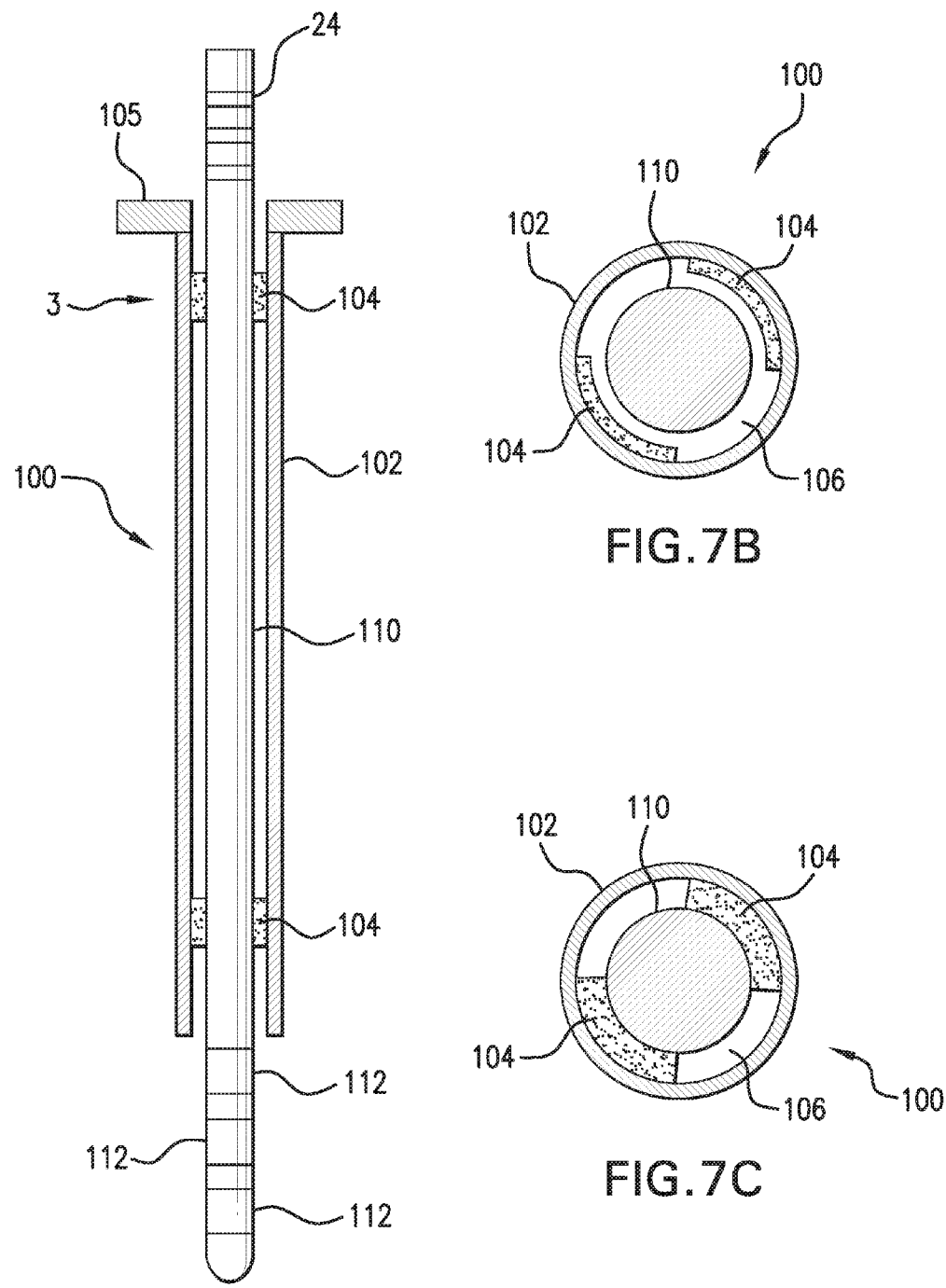

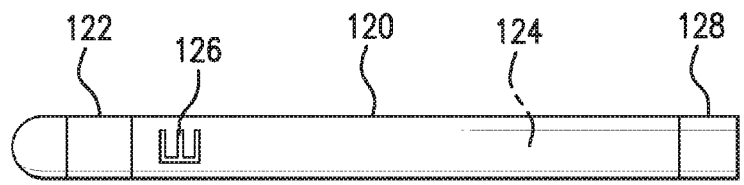
FIG.9A
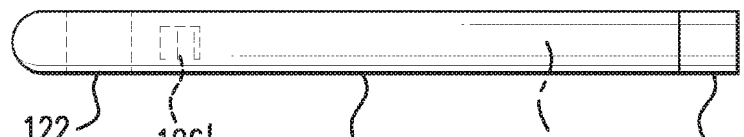
FIG.9B
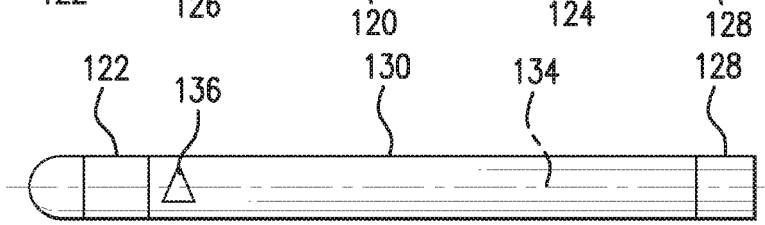
FIG.10A
FIG.10B
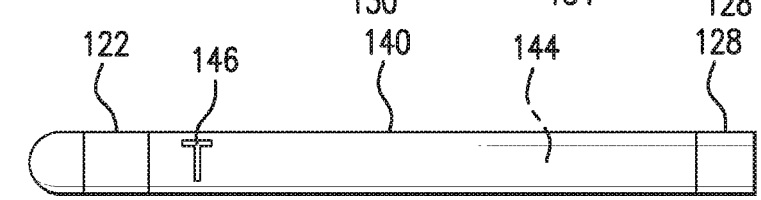
FIG.11A
FIG.11B
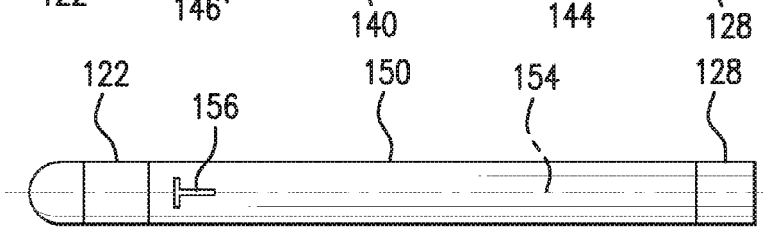
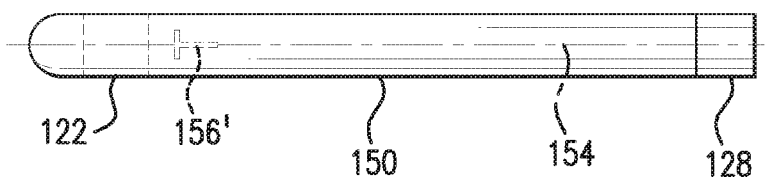
FIG.12A
FIG.12B

DIRECTIONAL ELECTRODE DEVICES WITH LOCATING FEATURES

CROSS-REFERENCE TO RELATED APPLICATIONS

This application is a divisional of U.S. patent application Ser. No. 12/029,141 filed Feb. 11, 2008, which is hereby incorporated by reference.

TECHNICAL FIELD

The present invention relates to medical devices, and in particular, electrode devices for electrical stimulation.

BACKGROUND

Implantable pulse generators for stimulating tissue are being used in increasing numbers to treat a wide variety of medical conditions. In many cases, electrical stimulation pulses are conveyed from a pulse generator to a desired stimulation site by an implanted lead with exposed electrodes. In order to achieve the desired effects from the delivery of stimulating pulses, it is important that the lead is properly positioned so that optimal stimulating energy is applied to a desired site. While this is true for many different kinds of stimulation therapies, lead positioning is especially critical in the area of neurological stimulation.

Stylets are used in the field of electrical stimulation for guiding and properly placing leads. Leads that utilize stylets for guidance are subject to the problem of lead twisting or torquing during placement. Lead twisting or torquing often results in the lead rotating with respect to the stylet and possibly becoming misaligned. Precise knowledge of the location and position of the lead and electrodes providing the stimulation, along with its volume of activation relative to the target site and surrounding structures is critical to treatments, particularly when providing neurological stimulation to an area of a patient's brain.

While conventional DBS systems have advanced rehabilitation and treatment in a number of areas, certain challenges remain and there is a need for electrode devices to meet these challenges.

SUMMARY

In a first aspect, the present invention provides an electrode assembly comprising: (a) an elongate lead having at least one directional electrode positioned at a distal portion thereof; and (b) a lead guide that is slidably engageable with the elongate lead in a coaxial relationship. The elongate lead and the lead guide are rotationally fixed when they are engaged with each other.

In a second aspect, the present invention provides an elongate lead comprising: (a) at least one directional stimulation electrode positioned on a distal portion of the elongate lead; and (b) at least one radiologically-visible feature for indicating the orientation of the at least one directional stimulation electrode when viewed under radiologic imaging.

In a third aspect, the present invention provides an electrode system comprising: (a) an elongate lead having at least one directional electrode positioned at a distal portion of the elongate lead; and (b) a position determining apparatus for determining the position and/or orientation of the at least one directional electrode when the electrode is positioned in a body.

In other aspects, the present invention provides methods for electrically stimulating a target site in the body using various electrode devices.

BRIEF DESCRIPTION OF THE DRAWINGS

FIG. 1A shows a side view of an elongate lead. FIG. 1B shows a side view of a stylet. FIG. 1C shows a side view of the elongate lead with the stylet inserted therein. FIG. 1D shows a transverse cross-section view of the assembly taken at arrow 1 in FIG. 1C.

FIG. 2A shows a perspective view of the stylet. FIG. 2B shows a distal end view of the stylet.

FIG. 3A shows a partial cross-section side view of the electrode assembly with an elongate lead inserted within a cannula. FIG. 3B shows a transverse cross-section view of the assembly taken at arrow 2 in FIG. 3A.

FIGS. 6A-6E show transverse cross-sections views of a stylet according to various alternate embodiments of the electrode assembly.

FIGS. 7A-7C show an electrode assembly according to yet another embodiment. FIG. 7A shows a partial cross-section side view of the assembly. FIG. 7B shows a transverse cross-section view of the assembly taken at arrow 3 in FIG. 7A, with the gripping elements in a released position. FIG. 7C shows a transverse cross-section view of the assembly taken at arrow 3 in FIG. 7A, with the gripping elements in a gripping position.

FIGS. 9A and 9B show side views of an elongate lead according to an embodiment of the present invention. FIG. 9A shows the elongate lead with the radiopaque feature facing out of the page. FIG. 9B shows the elongate lead rotated 180° from the view shown in FIG. 9A such that the radiopaque feature faces into the page.

FIGS. 10A and 10B show side views of an elongate lead according to another embodiment. FIG. 10A shows the elongate lead with the radiopaque feature facing out of the page. FIG. 10B shows the elongate lead rotated 180° from the view shown in FIG. 10A such that the radiopaque feature faces into the page.

FIGS. 11A and 11B show side views of an elongate lead according to yet another embodiment. FIG. 11A shows the elongate lead with the radiopaque feature facing out of the page. FIG. 11B shows the elongate lead rotated 180° from the view shown in FIG. 11A such that the radiopaque feature faces into the page.

FIGS. 12A and 12B show side views of an elongate lead having a radiopaque feature that is symmetric with respect to the central longitudinal axis of the elongate lead. FIG. 12A shows the elongate lead with the radiopaque feature facing out of the page. FIG. 12B shows the elongate lead rotated 180° from the view shown in FIG. 12A such that the radiopaque feature faces into the page.

FIG. 13A shows the elongate lead in a straight configuration. FIG. 13B shows the elongate lead in a twisted configuration.

FIG. 14A shows the elongate lead in one rotational orientation; and FIG. 14B shows the elongate lead rotated 180° from the view shown in FIG. 14A.

DETAILED DESCRIPTION

Figure 1A:
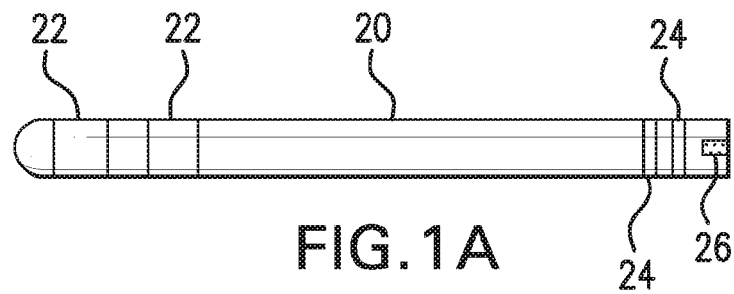
FIGS. 1A-1D show various views of an electrode assembly according to an embodiment of the present invention.

In an embodiment, the present invention provides methods, systems and devices for the accurate placement of leads in the brain and/or other parts of the nervous system. In a first aspect, the present invention provides an electrode assembly comprising a first component which is an elongate lead having at least one directional electrode positioned at a distal portion thereof. As used herein, a "directional electrode" refers to an electrode on an elongate lead in which the electrode extends less than 360° about the body of the elongate lead. The assembly further includes a second component that is a lead guide that is slidably engageable with the elongate lead in a coaxial relationship. Accordingly, the elongate lead may have an inner channel with the lead guide being insertable into the inner channel of the elongate lead; or alternatively, the lead guide may have an inner channel with the elongate lead being insertable into the inner channel of the lead guide. According to this embodiment, the elongate lead and the lead guide are rotationally fixed when they are engaged with one another. As used herein, the term "rotation," when used in relation to the elongate lead or the lead guide, refers to rotation about the central longitudinal axis of the component. By being rotationally fixed in relation to each other, rotation of the lead guide will cause rotation of the elongate lead, and vice versa. Similarly, if the lead guide is not rotated, this will cause non-rotation of the elongate lead. Accordingly, the elongate lead and the lead guide, although separate components, rotate as a single unit. Since the lead guide is designed to transfer any rotational torque (e.g., provided manually or by other means by the user at the proximal end of the lead guide) to the elongate lead, the lead guide may have any of various features for facilitating this function, such as handles and alignment markers indicating the alignment of the two components.

The rotational fixation between the elongate lead and the lead body may be achieved by any of various mechanisms to restrain rotational movement of the elongate lead in relation to the lead guide. Such mechanisms permit a rotational force placed on the proximal end of the lead guide to be transferred along the length of the lead thereby causing the proximal and distal ends of the lead to rotate together in unison. Non-limiting examples of locking mechanisms to achieve this restraint in rotational movement, include male/female connections, threadable engagement, or interference fit. In certain embodiments, the elongate lead comprises a first rotation locking structure, and the lead guide comprises a second rotation locking structure. The first rotation locking structure and the second rotation locking structure releasably engage and cooperate with each other to restrain rotational movement of the elongate lead in relation to the lead guide. The rotation locking structures may be located on any of various portions of the elongate lead or lead guide, including inner surfaces, outer surfaces, distal portions, or proximal portions so long as torque is transferred to the elongate lead when the lead guide is rotated. Therefore, lead guide and the elongate lead can be configured to be mated such that rotation of the proximal end of the lead guide causes the proximal and distal ends of the elongate lead to also rotate.

In some embodiments, the first rotation locking structure and the second rotation locking structure have complementary geometries (i.e. a male/female relationship), allowing a mating interaction between the two locking structures. For example, one component (i.e., the lead guide or the elongate lead) can have a protruding structure and the other component can have a recessed structure, wherein the protruding structure interlocks with the recessed structure in such a way as to limit rotational movement of the elongate lead relative to the lead guide. The protruding structures may be, for example, ridges, bumps, ribs, and the like. The recessed structure may be, for example, grooves, channels, pits, cavities, and the like. The female structure can either be part of the elongate guide or the lead body. Similarly, the male structure can be part of the elongate guide or the lead body. Furthermore, the locking structures can either be made of a separate material than the component to which they are a part of or they can be made of the same material. As such, the locking structures and their respective component can form a single unitary structure or the two can be separate elements that are coupled together.

Figure 1B:
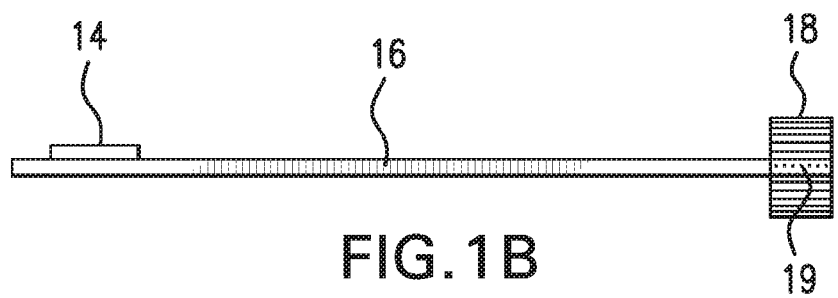
Figure 1C:
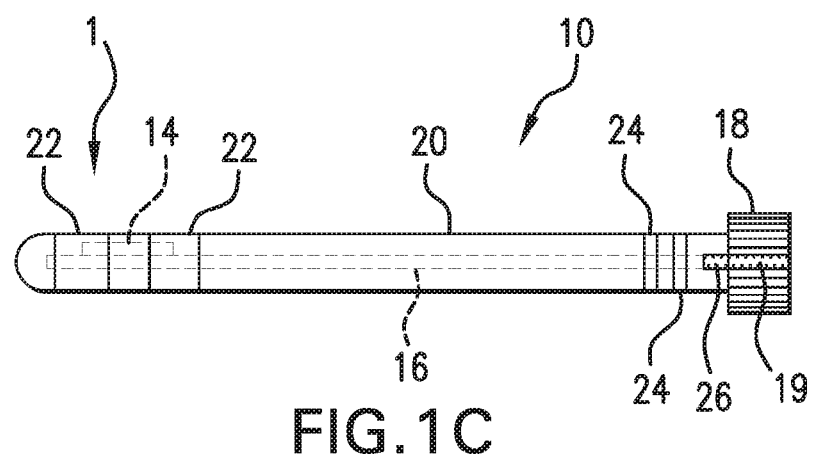
Figure 1D:
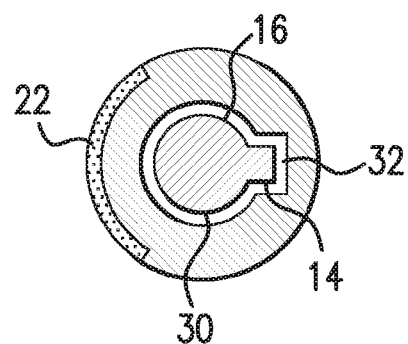

For example, referring to the embodiment shown in FIGS. 1A-1D, an electrode assembly 10 comprises an elongate lead 20 and a lead guide in the form of stylet 16. In this embodiment, elongate lead 20 has directional stimulation electrodes 22 positioned at a distal portion of elongate lead 20. As seen in FIG. 1D, directional electrodes 22 extend 120° about the body of elongate lead 20, however, the directional electrode can extend any degree about the body of lead 20 that is less than 360°. Elongate lead 20 also has electrical contacts 24 for coupling with an external stimulator or implantable pulse generator. Each of contacts 24 independently supply electrical connectivity to electrodes 22. Elongate lead 20 has an inner channel 30 which is configured to receive stylet 16. Stylet 16 is made of a relatively stiff material and is configured to be inserted within inner channel 30 of elongate lead 20. In this embodiment, the first rotation locking structure is a key 14 and is rigidly fixed onto or otherwise integral with a distal portion of stylet 16. Inner channel 30 of elongate lead 20 has the second locking structure, which is a recess 32 contoured to receive key 14 in a locking secure manner and which extends along the length of elongate lead 20. The recess can be made of the same material as the elongate lead, such as polyurethane, or can be a separate structure applied to the elongate lead, such as a metal insert. A handle 18 can be fixed to the proximal end of stylet 16 to allow the user to apply torque to stylet 16, which is transferred throughout the length of lead 20 thereby causing the proximal and distal ends of the lead to rotate in unison. Of course, stylet 16 could also be rotated by means other than manual means, such as electrically or telemetrically.

In operation, the distal end of elongate lead 20 is inserted into the target site. Stylet 16 is inserted into inner channel 30 of elongate lead 20. To ensure alignment of key 14 and recess 32, elongate lead 20 and stylet 16 can both have orientation indicators, which in the embodiment shown in FIGS. 1A-1C are marks parallel to the longitudinal axis of elongate lead 20 and stylet 16. Specifically, referring to FIGS. 1A-1C, the proximal end of elongate lead 20 can have an orientation indicator 26 and handle 18 of stylet 16 can have an orientation indicator 19, with orientation indicator 26 aligned with recess 32 and orientation indicator 19 aligned with key 14. When orientation indicator 26 is aligned with orientation indicator 19, a straight line is formed, which indicates that key 14 is aligned with recess 32. Of course, other configurations of orientation indicators 26 and 19 are also possible. Because of the mating of key 14 and recess 32, elongate lead 20 is rotationally locked with stylet 16. Thus, as elongate lead 20 is being positioned at the target site, the user can turn handle 18 of stylet 16 to cause elongate lead 20 to rotate accordingly, allowing the user to adjust the directional orientation of directional electrodes 22. One or more of directional electrodes 22 can then be activated to provide electrical stimulation to the target site.

Figure 2A:
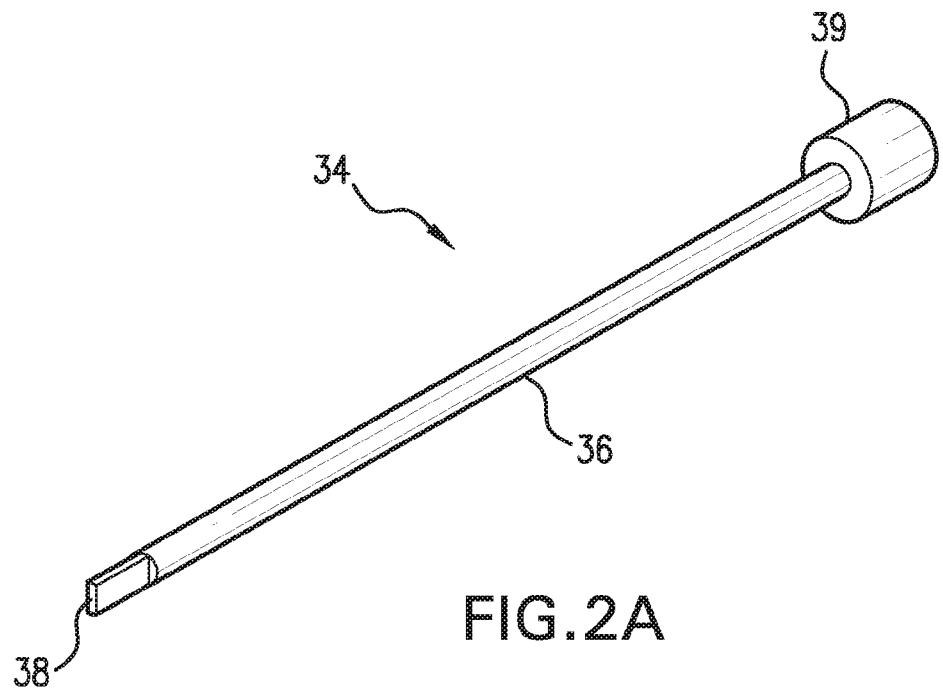
FIGS. 2A and 2B show a stylet according to another embodiment.
Figure 2B:
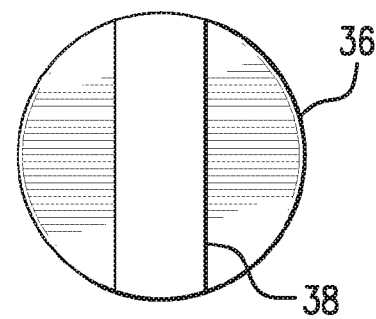

Other configurations for the stylet and/or key are also possible. For example, referring to the embodiment shown in FIGS. 2A and 2B, a stylet 34 has a shaft 36 and a key 38 located at the distal tip of shaft 36. As seen in the end-view of stylet 34 in FIG. 2B, in this embodiment, the maximum width of key 38 is no greater than the diameter of shaft 36. An elongate lead for use with stylet 34 can have a distally-located recess that is complementary to key 38.

Figure 3A:
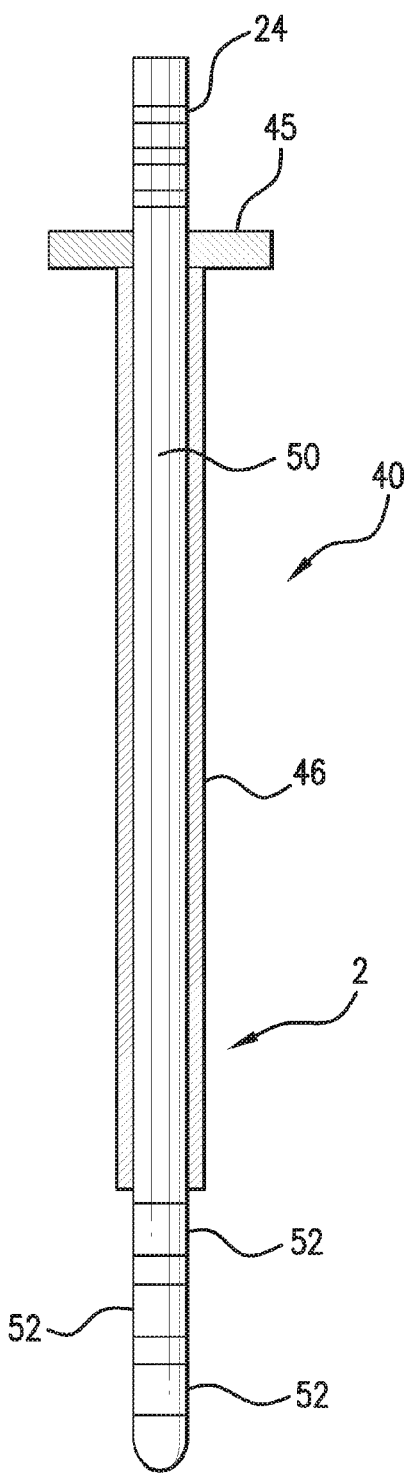
FIGS. 3A and 3B show an electrode assembly according to another embodiment.
Figure 3B:
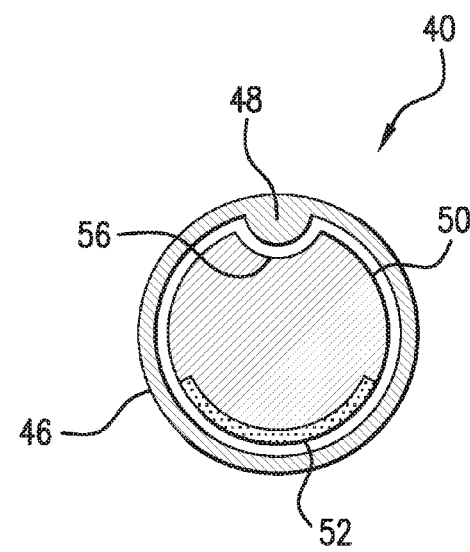

In another example of the electrode assembly, referring to the embodiment shown in FIGS. 3A and 3B, an electrode assembly 40 comprises an elongate lead 50 and a lead guide in the form of cannula 46. In this embodiment, the lead guide is disposed about the outer surface of the elongate lead, whereas in the embodiment illustrated in FIG. 1A-1D, the elongate lead is disposed about the outer surface of the lead guide. As with the embodiment described above, elongate lead 50 has directional stimulation electrodes 52 positioned at a distal portion of elongate lead 50. As seen in FIG. 3B, directional electrodes 52 extend 120° around the body of elongate lead 50, but can extend to other degrees less than 360° about the body of the lead. Elongate lead 50 also has electrical contacts 24 for coupling to an external stimulator or implantable pulse generator. Each of contacts 24 independently supply electrical connectivity to electrodes 52. On its outer surface, elongate lead 50 has a first rotation locking structure that is a groove 56 which is contoured to receive a second rotation locking structure that is a ridge 48 on the inside surface of cannula 46.

In this embodiment, cannula 46 has an inner channel configured to receive elongate lead 50. As stated above, on its inside surface, cannula 46 comprises a ridge 48 which extends along the length of cannula 46. Ridge 48 is contoured to mate with groove 56 of elongate lead 50 to form a locked relationship. A handle 45 can be fixed to the proximal end of cannula 46 to allow the user to manually rotate cannula 46. Of course, cannula 46 could also be rotated by other means, such as electrically or telemetrically.

In operation, the distal end of cannula 46 is inserted into the patient's body. Elongate lead 50 is inserted into the inner channel of cannula 46 such that groove 56 is aligned with ridge 48. Because of the mating of ridge 48 and groove 56, elongate lead 50 is rotationally locked with cannula 46. Thus, as elongate lead 50 is being positioned at the target site the user can turn handle 45 of cannula 46 to cause elongate lead 50 to rotate accordingly, allowing the user to adjust the directional orientation of directional electrodes 52. One or more of directional electrodes 52 can then be activated to provide electrical stimulation to the target site.

Figure 4:
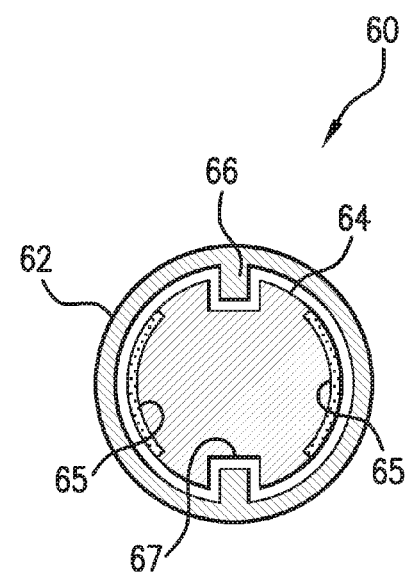
FIG. 4 shows a transverse cross-section view of an electrode assembly according to yet another embodiment.

In another example, referring to the embodiment shown in FIG. 4, an electrode assembly 60 comprises an elongate lead 64 and a lead guide in the form of a cannula 62. Cannula 62 has an inner channel configured to receive elongate lead 64. A pair of first rotational locking structures that are keys 66 are oppositely positioned on the inside surface of cannula 62. Keys 66 are contoured to mate with second locking structures, which are a pair of oppositely positioned grooves 67 on elongate lead 64. Grooves 67 are contoured to mate with keys 66 to form a locked relationship. Elongate lead 64 can have a pair of 120° directional stimulation electrodes 65 positioned on opposite sides of elongate lead 64. Of course, other directional electrodes can also be used. In operation, electrode assembly 60 is used in a manner similar to that described for the above-mentioned embodiments.

Figure 5:
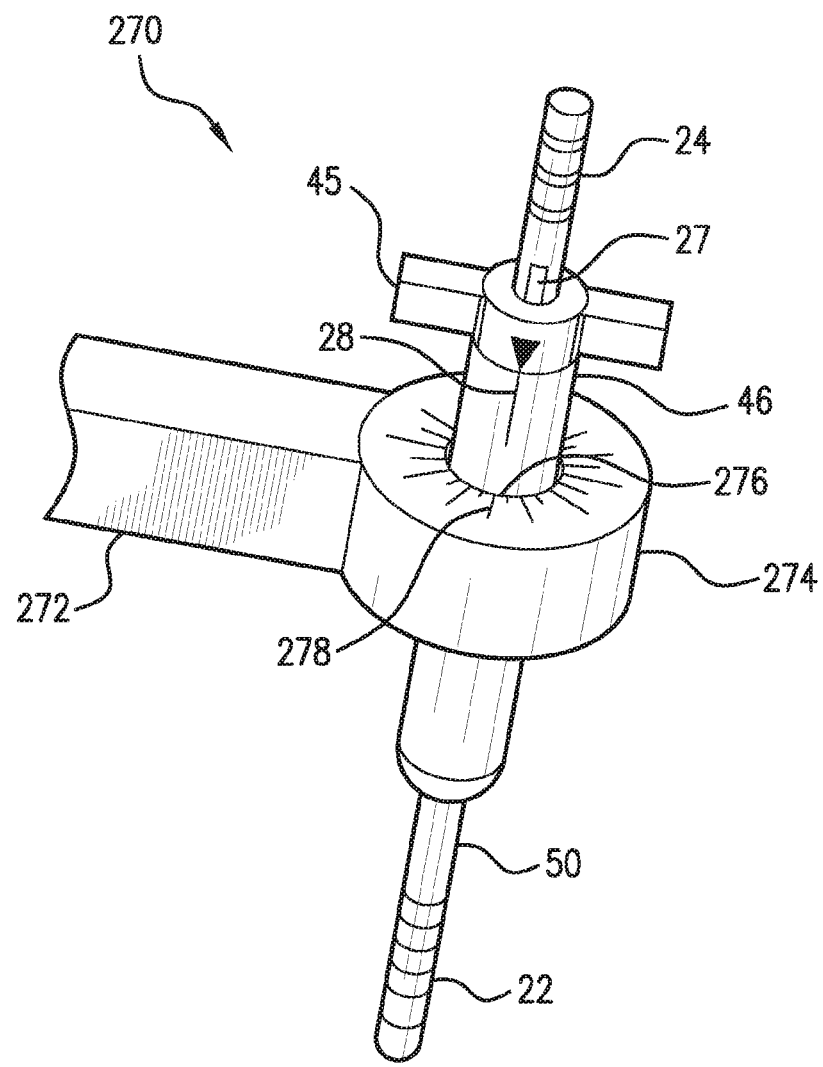
FIG. 5 shows a perspective view of a cannula holder according to an embodiment.

In some embodiments, the electrode assembly further comprises a lead guide holder for holding the lead guide. The lead guide holder has a rotational indicator that indicates the rotational orientation of the elongate lead and/or lead guide in relation to a fixed point of reference (e.g., a stereotactic headframe). For example, referring to the embodiment shown in FIG. 5, the electrode assembly of FIGS. 3A and 3B above may further include a cannula holder 270 which is moveably attached to a stereotactic headframe (not shown). As such, cannula holder 270 can move in various axes, directions, or rotational planes on the stereotactic headframe. Cannula holder 270 has an arm 272, which is attached to the stereotactic headframe, and a ring 274 with a bore 276 through which cannula 46 is inserted. On ring 274 are a series of evenly-spaced tics 278 positioned around the circumference of bore 276. Tics 278 indicate the rotational orientation of cannula 46 with respect to an orientation indicator 28 that is aligned with orientation indicator 27 on electrode lead 50. This orientation information may be entered into a coordinate mapping system (such as that described below) and used in combination with the fiducial parameters provided by the stereotactic headframe for mapping of the position and orientation of the elongate lead and/or electrode in relation to structures in the brain. Other rotational indicators could also be used for indicating the rotational orientation of the elongate lead and/or lead guide in relation to a fixed point of reference (e.g., a stereotactic headframe).

Of course other configurations of the first and second rotation locking structures are contemplated. In other words, any embodiments are contemplated where one of the components has a portion that can be securely attached to another portion of the other component to prevent rotational movement of one component relative to the other. For example, the stylet can have an irregularly shaped tip as the second rotation locking structure that locks into a receptacle, which serves as the first rotation locking structure, at the distal end of the elongate lead. The first and/or second rotation locking structures need not extend the entire length of the elongate lead.

FIGS. 6A-E show different non-circular cross-sectional shapes for at least a portion of a stylet and a corresponding receptacle of an elongate lead according to embodiments of the present invention. The cross-sections in FIGS. 6A-E are taken along a plane perpendicular to the longitudinal axis of the stylet. A rectangle 170, an ellipse 172, a square 174, a triangle 176 and a general triangular shape with a rounded surface 178 are shown in FIGS. 6A-E, respectively. Other non-circular cross sections may also be provided. These non-circular cross-sections, along with their corresponding receptacles, may extend the length of the stylet and/or elongate lead or may be provided at the proximal ends and/or the distal ends of the stylet and the elongate lead or may be provided at other locations such that a sufficiently uniform force is transferred along the length of the stylet to the elongate lead thereby causing the proximal ends and distal ends of the stylet and the elongate lead to rotate together. Accordingly, the ends of the stylet and the elongate lead do not become misaligned.

In certain embodiments, the lead guide comprises one or more gripping elements to provide the rotational fixation between the elongate lead and the lead guide. The gripping element(s) is designed to frictionally engage the elongate lead. In some embodiments, the lead guide further comprises an activation mechanism for causing the gripping elements to engage the elongate lead, to release the elongate lead, and/or to lock the gripping elements in their engaged or released positions. Any of various activation mechanisms may be used for this particular function, including mechanical (e.g., using a slide, pull, or button actuation), pneumatic, or hydraulic mechanisms.

For example, referring, to the embodiment shown in FIGS. 7A-7C, an electrode assembly 100 comprises an elongate lead 110 and a lead guide as cannula 102. Elongate lead 110 has directional stimulation electrodes 112 positioned at a distal portion of elongate lead 110 and contacts 24 at a proximal portion of elongate lead 110. Cannula 102 has an inner channel 106 configured to receive elongate lead 110. At proximal and distal portions, cannula 102 has a gripping elements 104 which are designed to frictionally engage elongate lead 110, thereby restraining rotational movement of elongate lead 110 relative to cannula 102. Referring to FIGS. 7B and 7C, the pair of proximally located gripping elements 104 are positioned on opposite sides of the inner surface of cannula 102. Likewise, the pair of distally located gripping elements 104 are also positioned on opposite sides of the inner surface of cannula 102. By an actuation mechanism (not shown), gripping elements 104 may alternately engage elongate lead 110 (see FIG. 7C) or release elongate lead 110 (see FIG. 7B). A handle 105 can be fixed to the proximal end of cannula 102 to allow the user to manually rotate cannula 102. Of course, the cannula could be rotated by other means as well.

In operation, the distal end of cannula 102 is inserted into the patient's body. With gripping elements 104 in the released position, elongate lead 110 is inserted into inner channel 106 of cannula 102. After further advancement and positioning of elongate lead 110 in the patient's body, the user can actuate gripping elements 104 to engage and rotationally fix elongate lead 110. Then, when the user turns handle 105 on cannula 102, elongate lead 110 will rotate accordingly, allowing the user to adjust the directional orientation of directional electrodes 112. One or more of directional electrodes 112 can then be activated to provide electrical stimulation to the target site.

Figure 8:
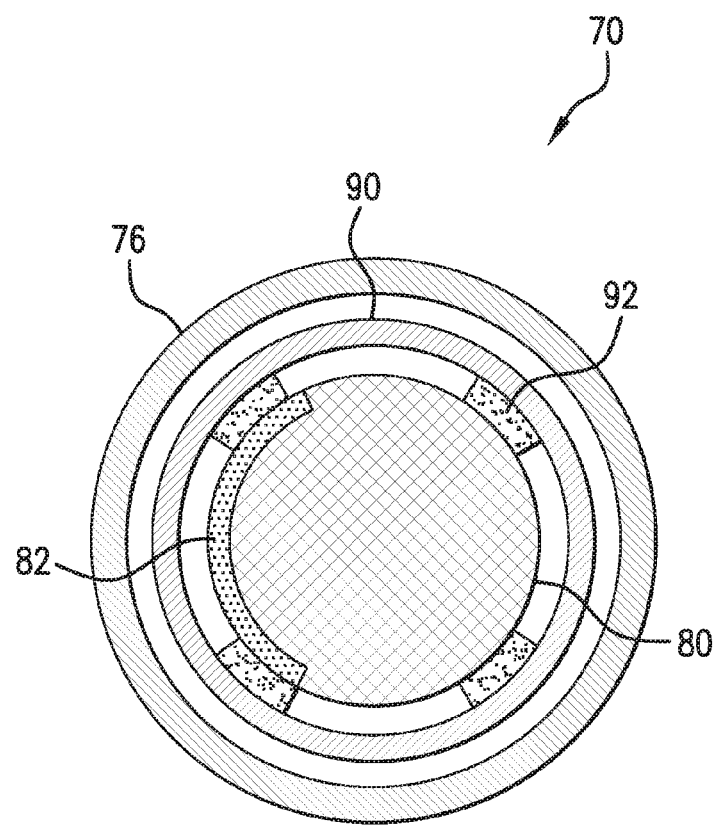
FIG. 8 shows a transverse cross-section view of an electrode assembly according to yet another embodiment.

In certain embodiments, the lead guide is a delivery structure that is designed to be positioned between the elongate lead and a cannula. The delivery system may engage the elongate lead using the mating mechanisms or gripping mechanisms described above. For example, referring to the embodiment shown in FIG. 8, an electrode assembly 70 comprises an elongate lead 80 and a lead guide as delivery structure 90. Cannula 76 has an inner channel configured to receive elongate lead 80 and delivery structure 90. Elongate lead 80 has a directional stimulation electrode 82 extending around the body of elongate lead 80. Delivery structure 90 is positioned between elongate lead 80 and cannula 76. As such, delivery structure 90 is configured to be insertable within the inner channel of cannula 76. Delivery structure 90 also has an inner channel which is configured to receive elongate lead 80. On its inner surface, delivery structure 90 has gripping elements 92 which frictionally engage elongate lead 80.

In operation, the distal end of cannula 76 is inserted into the patient's body. Then, delivery structure 90 (containing elongate lead 80, which is frictionally engaged with delivery structure 90 through gripping elements 92) is inserted into the inner channel of cannula 76. Because delivery structure 90 is rotationally locked with elongate lead 80, the user can turn delivery structure 90 to cause elongate lead 80 to rotate in concert accordingly, allowing the user to adjust the directional orientation of directional electrode 82. Directional electrode 82 can then be activated to provide electrical stimulation to the target site.

In an alternate embodiment, delivery structure 90 may have additional gripping elements which frictionally engage cannula 76. In this case, cannula 76 is rotationally locked with delivery structure 90, which in turn, is rotationally locked with elongate lead 80. As such, the user can turn cannula 76 to cause elongate lead 80 to rotate in concert, allowing the user to adjust the directional orientation of directional electrode 82.

The gripping element(s) may have any of various shapes, sizes, configurations, textures, and material compositions suitable for performing the above-described function. For example, the gripping element(s) may be formed of a deformable material, such as a soft thermoplastic material (e.g., silicone or polyurethane) and shaped to conform to the contours of the elongate lead. Alternatively, the gripping elements could comprise a more rigid base that is padded with a softer material such as silicone or polyurethane to prevent damage to the lead.

The gripping element(s) may be located at any of various positions on the lead guide, including the outer surface, proximal portions, or distal portions of the lead guide. The gripping element(s) and the lead guide may form a single unitary structure, or the two components may be separate units that are coupled together. Further, when more than one gripping element is employed, the gripping elements can be placed in different positions relative to each other so long as they collectively perform their intended function. For example, two or more gripping elements may be arranged in opposition to each other such that they engage opposite sides of the elongate lead, or the gripping element(s) may circumferentially surround the elongate lead.

This first aspect of the present invention may be combined with any of the features in the second and/or third aspects of the present invention.

In a second aspect, the present invention provides an elongate lead having one or more radiologically-visible features that indicate the rotational orientation of the directional electrode under radiologic imaging. The radiologically-visible feature may be radiolucent, radiopaque, or otherwise, so long as the feature is visible under radiologic imaging. The radiologic imaging may be any of various imaging modalities that are used to view an object inserted into a patient's body, including x-ray, x-ray fluoroscopy, CT scan, or MRI.

In certain embodiments, the radiologically-visible feature has a shape that is asymmetric with respect to the central longitudinal axis of the elongate lead. By having a shape that is asymmetric with respect to the central longitudinal axis of the elongate lead, the image of the feature under radiologic imaging will vary with the rotation of the elongate lead with respect to the particular view. For example, when viewed directly face-on, the feature will have one image; and when the elongate lead is rotated 180°, the see-through view of the feature will have a different (flipped) image. This allows the user to determine and/or adjust the rotational orientation of the directional electrode under radiologic imaging.

For example, referring to the embodiment shown in FIGS. 9A and 9B, an elongate lead 120, with a central longitudinal axis 124, has a radiopaque feature in the form of marking 126 which is asymmetric with respect to central longitudinal axis 124. Elongate lead 120 has a directional stimulation electrode 122 that extends 120° around the body of elongate lead 120 and an electrical contact 128 to supply electrical connectivity to electrode 122. In FIG. 9A, elongate lead 120 is rotated such that directional electrode 120 is facing out of the page (i.e., direct face-on view), and in FIG. 9B, elongate lead 120 is rotated 180° such that directional electrode 122 is facing into the page (i.e., see-through view). As such, the image of marking 126 seen in FIG. 9A is different from the flipped image 126' of marking 126 see in FIG. 9B. In operation, elongate lead 120 is positioned in the body and viewed under x-ray fluoroscopy. Since marking 126 is aligned with directional electrode 122, by visualizing marking 126 at various viewpoints under x-ray fluoroscopy, the user is able to determine the orientation of directional electrode 122 and make any necessary adjustments. Directional electrode 122 is then activated to provide electrical stimulation to the target site.

In another example, referring to the embodiment shown in FIGS. 10A and 10B, an elongate lead 130 has a central longitudinal axis 134, a marking 136 which is asymmetric with respect to central longitudinal axis 134, a directional electrode 122, and an electrical contact 128 to supply electrical connectivity to electrode 122. FIG. 10A shows a direct face-on view of marking 136, and FIG. 10B shows a see-through image 136' of marking 136 when elongate lead 130 is rotated 180°. In another example, referring to the embodiment shown in FIGS. 11A and 11B, an elongate lead 140 has a central longitudinal axis 144 and a marking 146 which is asymmetric with respect to central longitudinal axis 144. FIG. 11A shows a direct face-on view of marking 146, and FIG. 11B shows a see-through image 146' of marking 146 when elongate lead 140 is rotated 180°. Of course, the above described asymmetric features are only exemplary and other asymmetric features could also be used. For example a "C" shaped feature could also be used.

In a comparative example, referring to FIGS. 12A and 12B, a marking 156 is symmetric with respect to the central longitudinal axis 154 of elongate lead 150. The direct face-on view of marking 156 in FIG. 12A is identical to the see-through image 156' of marking 156 when elongate lead 150 is rotated 180°.

Figure 13A:
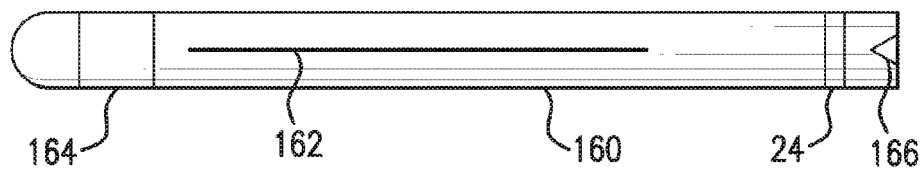
FIGS. 13A and 13B show side views of an elongate lead according to yet another embodiment.

In certain embodiments, the radiologically-visible feature(s) provides an image that becomes distorted when a proximal portion of the elongate lead is rotationally misaligned with a distal portion of the elongate lead (i.e., the elongate lead is twisted). By viewing the radiologic image of the radiologically-visible feature, the user can determine if there is any misalignment between proximal and distal portions of the elongate lead. For example, referring to the embodiment shown in FIGS. 13A and 13B, an elongate lead 160 has a directional stimulation electrode 164 at its distal portion and an electrical contact 24 to provide electrical connectivity to directional electrode 164. Elongate lead 160 also has an orientation indicator 166 which is aligned with the orientation of directional electrode 164. Elongate lead 160 also has a radiopaque feature in the form of a radiopaque stripe mark 162 on the surface of elongate lead 160.

Figure 13B:
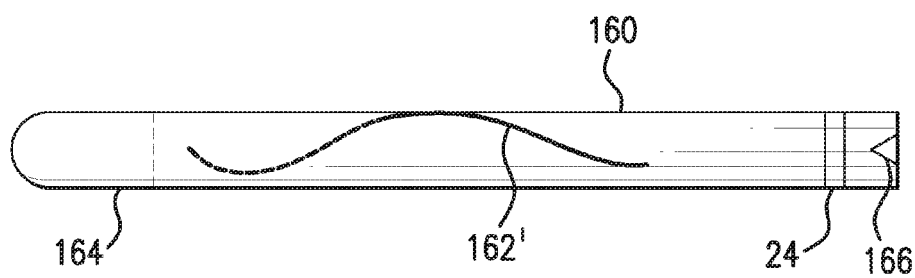

In operation, elongate lead 160 is inserted into the body and rotated at its proximal end to place electrode 164 in the desired orientation based on the alignment of orientation indicator 166. However, if rotational movement at the proximal end of elongate lead 160 is not fully translated to corresponding rotational movement at the distal end, the resulting twisting in elongate lead 160 will cause orientation indicator 166 to be misaligned with directional electrode 164. When viewed under x-ray fluoroscopy, as shown in FIG. 13B, it will be apparent that twisting in elongate lead 160 has caused stripe mark 162 to form a distorted image 162'. On this basis, the user will be aware of the twisting in elongate lead 160 and take appropriate action. Directional electrode 164 is then activated to provide electrical stimulation to the target site.

Figure 14A:
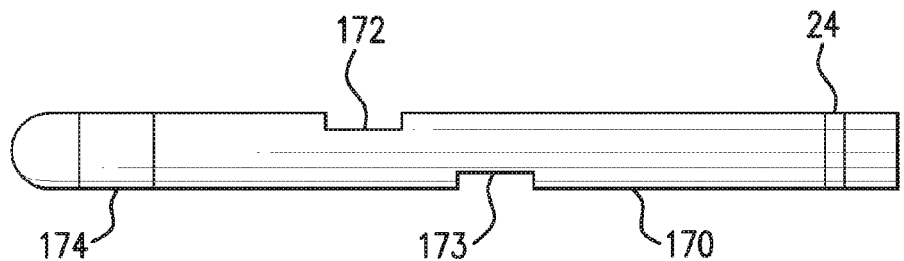
FIGS. 14A and 14B show side views of an elongate lead according to yet another embodiment.
Figure 14B:
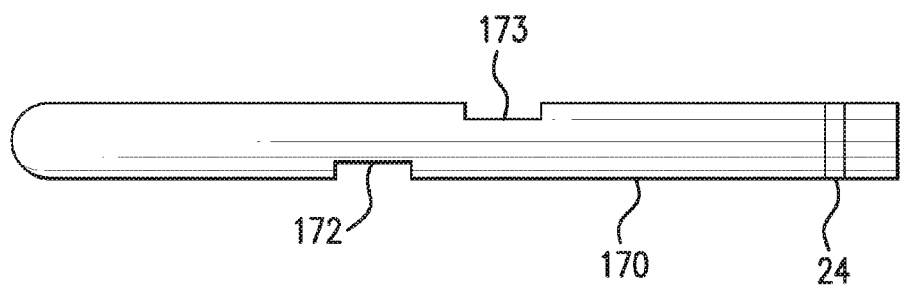

In some cases, the radiologically-visible feature is radiolucent. For example, referring to the embodiment shown in FIGS. 14A and 14B, an elongate lead 170 has a directional simulation electrode 174 at its distal portion and an electrical contact 24 to provide electrical connectivity to directional electrode 174. Elongate lead 170 also has two radiolucent cut-out windows, 172 and 173, that are adjacently positioned on opposite sides of elongate lead 170. FIG. 14A shows elongate lead 170 in one rotational orientation and FIG. 14B shows elongate lead 170 rotated 180° from the view shown in FIG. 14A. Based on the positions of radiolucent cut-out windows 172 and 173 under radiologic imaging, a user can determine the orientation of elongate lead 170 and/or directional electrode 174.

The radiologically-visible feature(s) may also be positioned anywhere along the length of the elongate lead, including proximal and distal portions. In some cases, the elongate lead may have two or more radiologically-visible features which are positioned in such a manner (e.g., alternating or staggered configurations) for more accurate determinations of orientation.

The material used to form the radiopaque feature(s) may be any of various radiopaque materials, such as metallic materials or semi-metallic materials. Non-limiting examples of materials include titanium dioxide, bismuth compounds, or barium sulfate. The radiopaque feature(s) can be affixed to the elongate lead in any of various ways, including applying as a surface marking, embedding within the wall of the elongate lead, or inserting within the elongate lead.

This second aspect of the present invention may be combined with any of the features in the first and/or third aspects of the present invention.

In any of the embodiments described above, the size, shape, configuration, and dimensions of the elongate lead will vary depending upon the particular application. For example, the shape of the elongate lead may be cylindrical, flat, conical, etc. Where the elongate lead is cylindrical, the diameter of the elongate lead may be in the range of about 0.5 to 1.50 mm, but other diameters are also possible, depending upon the particular application. The length of the elongate lead may be in the range of about 10 to 60 cm, but other lengths are also possible, depending upon the particular application. In some cases, the size, shape, configuration, and dimensions of the elongate lead are selected for use in electrical stimulation of brain structures. For example, co-pending application Ser. No. 10/602,319 (filed Jun. 24, 2003) describes various stimulation leads and electrodes which are suitable for use in the present invention. The material composition and mechanical properties (i.e. the flexibility) of the body of the elongate lead will vary depending upon the particular application. In some cases, the body of the elongate body is formed of a non-conductive material, such as a polymeric material, glass or quartz including silicone and/or polyurethane.

In any of the embodiments described above, the elongate lead has at least one stimulation electrode positioned at a distal portion of the elongate lead. The stimulation electrode is designed to provide electrical stimulation to a part of a patient's body (e.g., parts of the brain). As mentioned above, the stimulation electrodes are directional electrodes that extend less than 360° about the body of the elongate lead. This means that the stimulation electrode bands do not form a continuous electrode surface, but rather the electrode bands are segmented into a plurality of individual electrodes that are substantially isolated from each other. Individual electrodes can range in an angular distance around the exterior of the body of the elongate lead by as little as a few degrees to almost completely around the body of the lead. The radial span of the electrodes can be, for example, 120° about the body of the elongate lead. Of course, the elongate lead can also include, in addition to one or more directional electrodes, cylindrical electrodes that extend 360° about the body of the lead. Where the elongate lead has multiple electrodes, the electrodes may be electrically isolated from each other and electively activated. This selective powerability of the electrodes provides a desired, focused (i.e. directed) electrical field around the body of the lead. The material composition, electrical properties (e.g., impedance), dimensions (e.g., height, width, axial spacing, and shape), and number (e.g., single or multiple) of the stimulation electrodes on the elongate lead will vary depending upon the particular application. For example, the electrodes may have a cylindrical shape, an oval shape, or a rectangular shape. In fact, the individual electrodes may take any variety of shapes to produce the desired focused and/or directional electric field.

In any of the embodiments described above, the lead guide and the delivery structure may have any of various shapes, sizes, dimensions, mechanical properties (e.g., stiffness), and material compositions, depending upon the particular application. For example, the lead guide and/or the delivery structure may be made of tungsten, stainless steel, MP35N, and may be coated with PTFE, parylene, or ETFE. The lead guide should be rigid enough such that the distal end of the lead guide moves in unison with the proximal end when the lead guide is rotated. Similarly, the delivery structure should be rigid enough such that the distal end of the delivery structure moves in unison with the proximal end when the delivery structure is rotated.

In a third aspect, the present invention provides an electrode system for determining the position and/or rotational orientation of an electrode positioned within a body. The system comprises an elongate lead having at least one directional electrode positioned at a distal portion of the elongate lead and a position determining apparatus for determining the position and/or orientation of the electrode when the electrode is positioned in a body.

Any of various types of apparatuses for determining the position of a remote object can be used in the electrode system. The position and/or orientation may be determined within a one-dimensional, two-dimensional, or three-dimensional framework. In certain embodiments, the system uses remote signal detection for determining the position and/or orientation of an electrode. The remote signal may emitted from the electrode itself, or may be emitted from the body tissue being stimulated by the electrode (for example, brain waves that can be captured by EEG). As such, the position determining apparatus comprises a plurality of signal detection sensors, positioned externally (for example, on the scalp) or internally to the patient's body (for example, subcutaneously or on the cortex), for detecting the desired signal. The number and spatial positions of the signal detection probes will depend upon various conditions, such as the location of the target site, the strength of the signal, the desired resolution, and the desired number of positional axes (1-D, 2-D, or 3-D).

In some cases, the system comprises three or more signal detection probes to allow for triangulation of the electrode. For example, by triangulation based on the differential strengths of the detected signals from three signal detection probes (which will vary according to the distance of the signal detection probes from the signal), the x, y, z coordinates and the orientation of the electrode can be calculated. Any of various types of signal processing systems and computer systems can be used to process the signal and perform the mathematical calculations for determining the position and/or orientation of the electrode.

Figure 15:
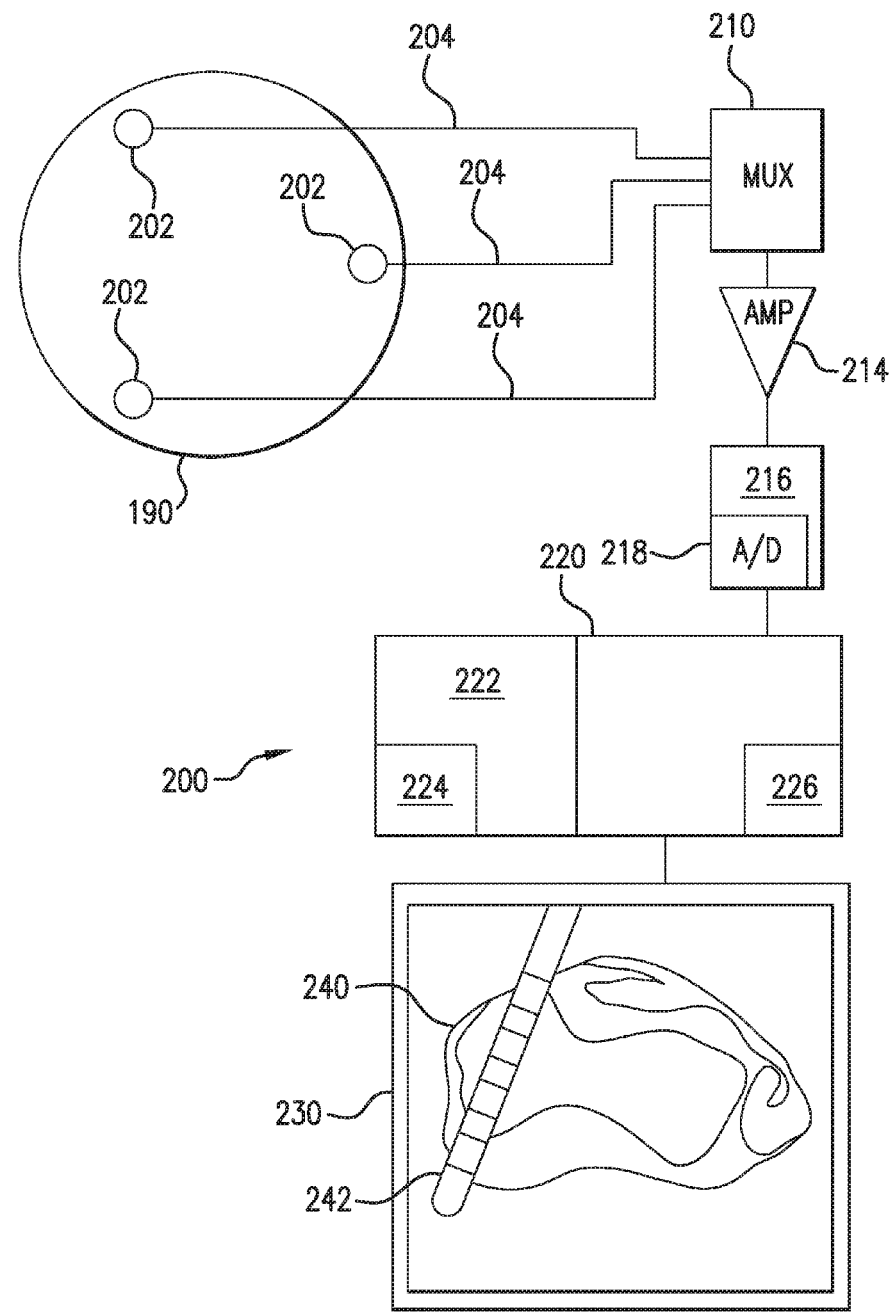
FIG. 15 shows an electrode system according to an embodiment of the present invention.

For example, referring to the embodiment shown in FIG. 15, an electrode system 200 comprises three EEG sensors 202 located on pre-determined spatial positions on the top of a patient's head 190. Each of EEG sensors 202 are electrically coupled via wires 204 to separate input channels of a conventional multiplexer 210, which samples each sensor input channel in a time-multiplexed fashion. The selected EEG sensor signal is then input into an amplifier 214 and the amplified signal is sent to a signal processor 216 to process the signal. Signal processor 216 contains an analog-to-digital converter (A/D) 218 to convert the signals into digital form, which is then transmitted to a conventional computer 220 or clinician and/or patient programmer containing a microprocessor 226 and memory 222. Alternatively, a conventional EEG apparatus may be used in combination with the electrode system, with the EEG data being stored and then transferred to the electrode system.

Memory 222 is loaded with software 224 which is configured to establish an orthogonal three-dimensional coordinate system and receive spatial information about the relevant anatomic structures and/or other fiducial references, which is then stored in memory 222. Software 224 also receives and stores information about the spatial positioning of EEG sensors 202. Using any of various triangulation algorithms, software 224 then uses the signal data to calculate the position and/or orientation of the electrode inside the brain. A mapping function is then used to translate the calculated position and/or orientation into the reference frame of the stored coordinate system containing the fixed anatomic structures and/or other fiducial references (e.g., the AC-PC plane of the brain, or the neurosurgical stereotactic headframe). A three-dimensional composite image, showing a lead 240 and electrodes 242, is then displayed on a display screen 230. This three-dimensional image can be manipulated to provide various views, including coronal, sagittal, and axial views. In some cases, the volume of activation provided by electrodes 242 may also be displayed in conjunction with the relevant brain structures. This allows the user to adjust the orientation and/or position of lead 240, or adjust various stimulation parameters such as signal intensity or amplitude, to specifically target the relevant brain structures.

Figure 16:
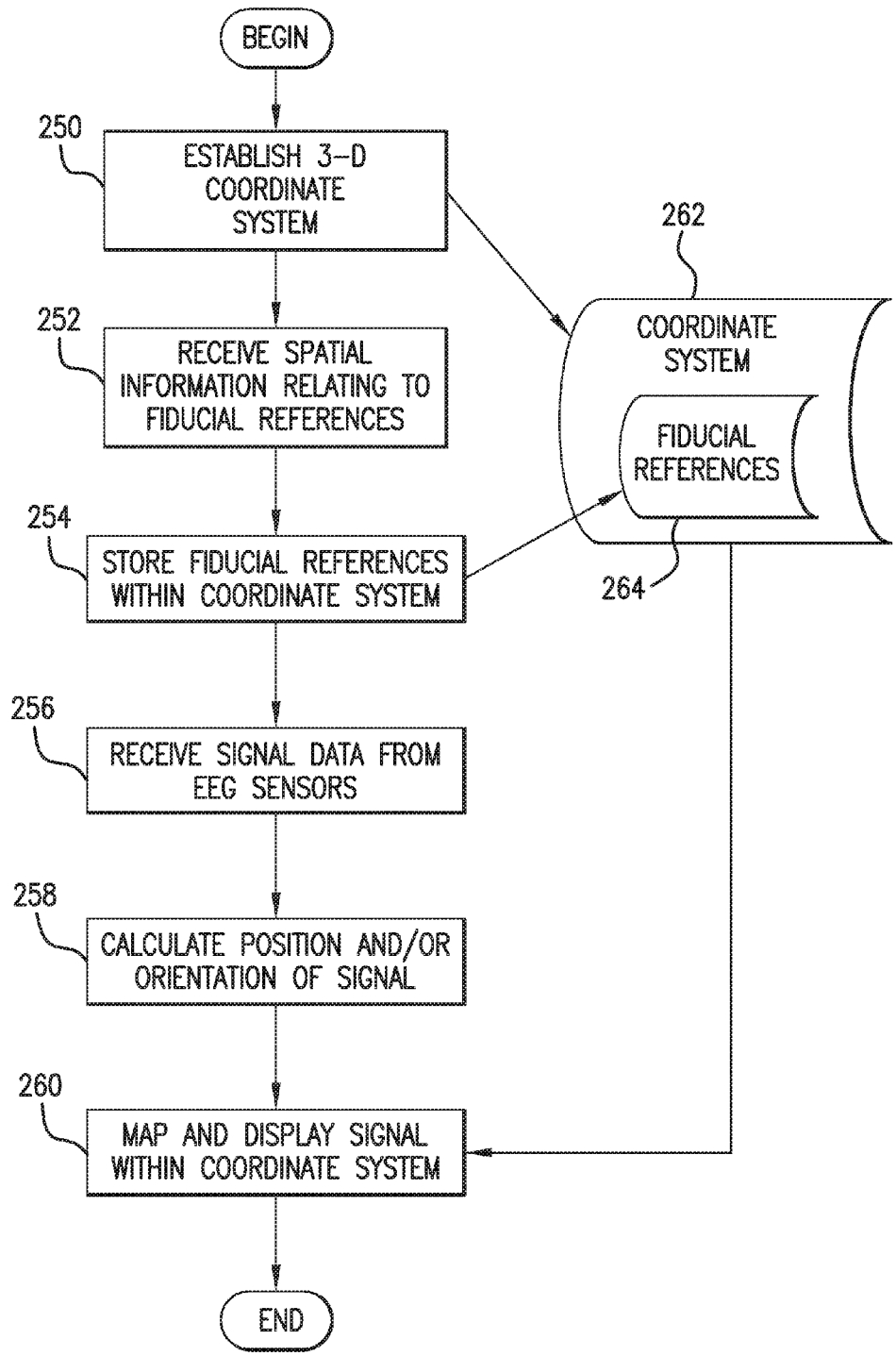
FIG. 16 shows a flowchart illustrating the processes performed by software within an electrode system according to yet another embodiment.

The flowchart in FIG. 16 illustrates the above-mentioned processes performed by software 224. Namely, software 224 establishes an orthogonal 3-D coordinate system (process blocks 250 and 262); receives spatial information about the fiducial references (process block 252); stores the fiducial references within the coordinate system (process blocks 254 and 264); receives signal data from the EEG sensors (process block 256); calculates the position and/or orientation of the signal (process block 258); and, maps and displays the signal within the stored coordinate system (process blocks 260 and 262).

In certain embodiments, the position determining apparatus uses any of various electromechanical position transducers for determining the position of the electrode based on the movement of the elongate lead and/or lead guide. For example, the linear motion actuation systems and/or navigation systems described in co-pending application Ser. No. 10/602,319 (filed Jun. 24, 2003) may be used in the position determining apparatus. Any of various types of signal processing systems and computer systems, including those mentioned above, can be used to process the signal and perform the mathematical calculations for determining the position and/or orientation of the electrode.

In certain embodiments, the position determining apparatus comprises a sensing electrode positioned on the elongate lead. The sensing electrode has an impedance suitable for detecting and/or recording an electrical signal from neural structures in the brain. Based on the characteristics of signals emitted by different neural structures, and by comparing with the electrical signals detected by the sensing electrodes, the position and/or orientation of the elongate lead may be determined. Any of various types of signal processing systems and computer systems, including those mentioned above, can be used to process the signal and perform the mathematical calculations for determining the position and/or orientation of the electrode.

In certain embodiments, the position determining apparatus comprises a computer system with a user interface for receiving manually inputted data which can be used to calculate the position and/or orientation of the electrode. For example, the position determining apparatus may receive manually inputted data for the location of the tip of the elongate lead (for example, as indicated by the stereotactic headframe), the rotational orientation of the elongate lead (for example, using the cannula holder shown in FIG. 5), and the angle of entry of the elongate lead (for example, as indicated by the stereotactic headframe via arc and ring coordinates). The system can then use this data to map the position and/or orientation into a coordinate system containing the fixed anatomic structures and/or other fiducial references (e.g., the AC-PC plane of the brain, or the neurosurgical stereotactic headframe).

This third aspect of the present invention may be combined with any of the features in the first and/or second aspects of the present invention.

The present invention may have any of various applications in electrical stimulation treatments. For example, in addition to brain stimulation, the present invention may be used for delivering electrical stimulation to the spinal cord, spinal nerve roots, ganglions, and other structures of the nervous system.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. An assembly, comprising:
an elongate lead having a central longitudinal axis, a distal portion, a proximal portion, and at least one directional electrode positioned on the distal portion of the elongate lead; and
a lead guide that is slidably engageable with the elongate lead in a coaxial relationship and facilitates placement of the elongate lead within tissue of a patient, wherein the lead guide is a cannula or a stylet;
wherein the elongate lead and the lead guide are rotationally fixed when they are engaged with each other, wherein the elongate lead has a first orientation indicator and the lead guide has a second orientation indicator, and wherein the first orientation indicator aligns with the second orientation indicator when the elongate lead and the lead guide are engaged with each other.

2. The assembly of claim 1, wherein the lead guide is the cannula and the lead guide has an inner channel for slidably receiving the elongate lead.

3. The assembly of claim 2, wherein the lead guide comprises one or more gripping elements for frictionally engaging the elongate lead.

4. The assembly of claim 3, wherein the one or more gripping elements comprises a pair of proximally located gripping elements disposed on opposite sides of the inner channel of the cannula.

5. The assembly of claim 4, Wherein the one or more gripping elements further comprises a pair of distally located gripping elements disposed on opposite sides of the inner channel of the cannula.

6. The assembly of claim 1, wherein the elongate lead comprises a first rotation locking structure, wherein the lead guide comprises a second rotation locking structure, and wherein the first rotation locking structure and the second rotation locking structure are configured to engage each other.

7. The assembly of claim 6, wherein the lead guide is the cannula and the first rotation locking structure is a groove and the second rotation locking structure is a key or a ridge.

8. The assembly of claim 6, wherein the lead guide is the cannula and the first rotation locking structure is a plurality of grooves and the second rotation locking structure is a plurality of keys or ridges.

9. The assembly of claim 6, wherein the lead guide is the stylet and the first rotation locking structure is a recess and the second rotation locking structure is a key.

10. The assembly of claim 1, wherein the lead guide is the stylet and the elongate lead has an inner channel for slidably receiving the lead guide.

11. The assembly of claim 10, wherein the stylet has an irregularly shaped tip and the lead comprises a receptacle into which the irregularly shaped tip locks.

12. The assembly of claim 1, further comprising a delivery structure having an inner channel for receiving the elongate lead, and wherein the lead guide is the cannula and has an inner channel for receiving the delivery structure.

13. The assembly of claim 12, wherein the delivery structure comprises one or more gripping elements for frictionally engaging the elongate lead and the lead guide.

14. The assembly of claim 1, further comprising a lead guide holder that holds the lead guide, wherein the lead guide holder has a rotational indicator.

15. The assembly of claim 14, wherein the lead guide holder comprises a ring having the rotational indictor.

16. The assembly of claim 1, wherein the elongate lead and the lead guide are rotationally fixed via a male/female connection.

17. The assembly of claim 1, wherein the elongate lead and the lead guide are rotationally fixed via a threadable engagement.

18. The assembly of claim 1, wherein the elongate lead and the lead guide are rotationally fixed via an interference fit.

19. The assembly of claim 1, wherein the lead guide is the stylet and the first orientation indicator is a first mark on the lead and the second orientation indicator is a second mark on the stylet.

20. The assembly of claim 1, Wherein the lead guide is the cannula and the first orientation indicator is a first mark on the lead and the second orientation indicator is a second mark on the cannula.

* * * * *